United States Patent [19]

Albert

[11] 4,144,457
[45] Mar. 13, 1979

[54] TOMOGRAPHIC X-RAY SCANNING SYSTEM

[76] Inventor: Richard D. Albert, 317 Hartford Rd., Danville, Calif. 94526

[21] Appl. No.: 674,059

[22] Filed: Apr. 5, 1976

[51] Int. Cl.² ............................................. A61B 6/02
[52] U.S. Cl. .......................... 250/445 T; 250/416 TV
[58] Field of Search ................ 250/416 TV, 363, 366, 250/445 T

[56] References Cited

U.S. PATENT DOCUMENTS

| | | | |
|---|---|---|---|
| 2,667,585 | 1/1954 | Gradstein | 250/416 TV |
| 3,778,614 | 12/1973 | Hounsfield | 250/363 |
| 3,780,291 | 12/1973 | Stein et al. | 250/363 |
| 3,919,556 | 11/1975 | Berninger | 250/366 |
| 4,002,917 | 1/1977 | Mayo | 250/445 T |
| 4,010,370 | 3/1977 | Lemay | 250/366 |
| 4,031,395 | 6/1977 | Lemay | 250/360 |

*Primary Examiner*—Craig E. Church
*Assistant Examiner*—T. N. Grigsby
*Attorney, Agent, or Firm*—Phillips, Moore, Weissenberger, Lempio & Majestic

[57] ABSTRACT

Cross-sectional or oblique sectional tomographic X-ray images of a subject are obtained more quickly, easily and economically and with less cumbersome apparatus by utilizing an X-ray source in which a moving point source of X-rays is produced by sweeping an electron beam across a broad anode plate. One or more relatively small X-ray detectors are situated on the opposite side of the subject to produce X-ray counts in the course of the scanning action, the counts being indicative of variations of X-ray transmissiveness within a plane extending crosswise or obliquely through the subject. By repetitively shifting the angular relationship of the subject relative to the X-ray source and detector structure and repeating the scanning process between each such angular movement, data is obtained which is used to generate a visible cross-sectional image of the subject. By repeating the scanning process in a series of adjacent planes, data for generating a three-dimensional X-ray image of the subject may also be obtained. Processing of the X-ray detector output signals and scan position data to produce the desired images may be done using digital computer techniques or by analog apparatus.

32 Claims, 16 Drawing Figures

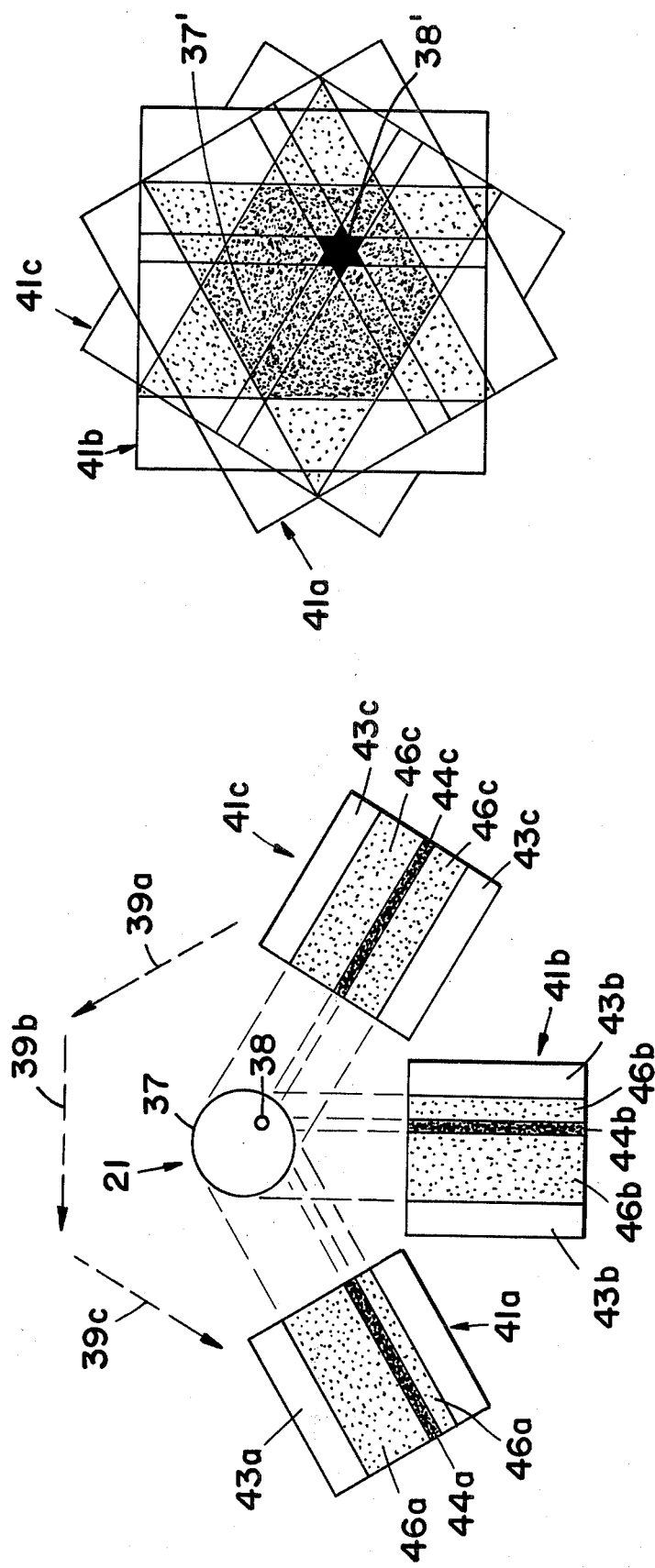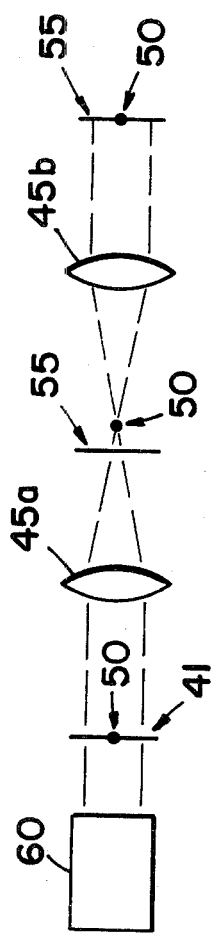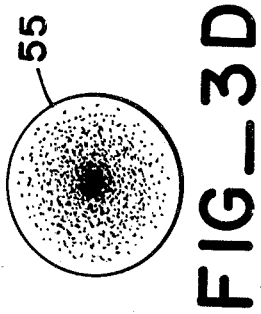
FIG_3A
FIG_3B
FIG_3C
FIG_3D

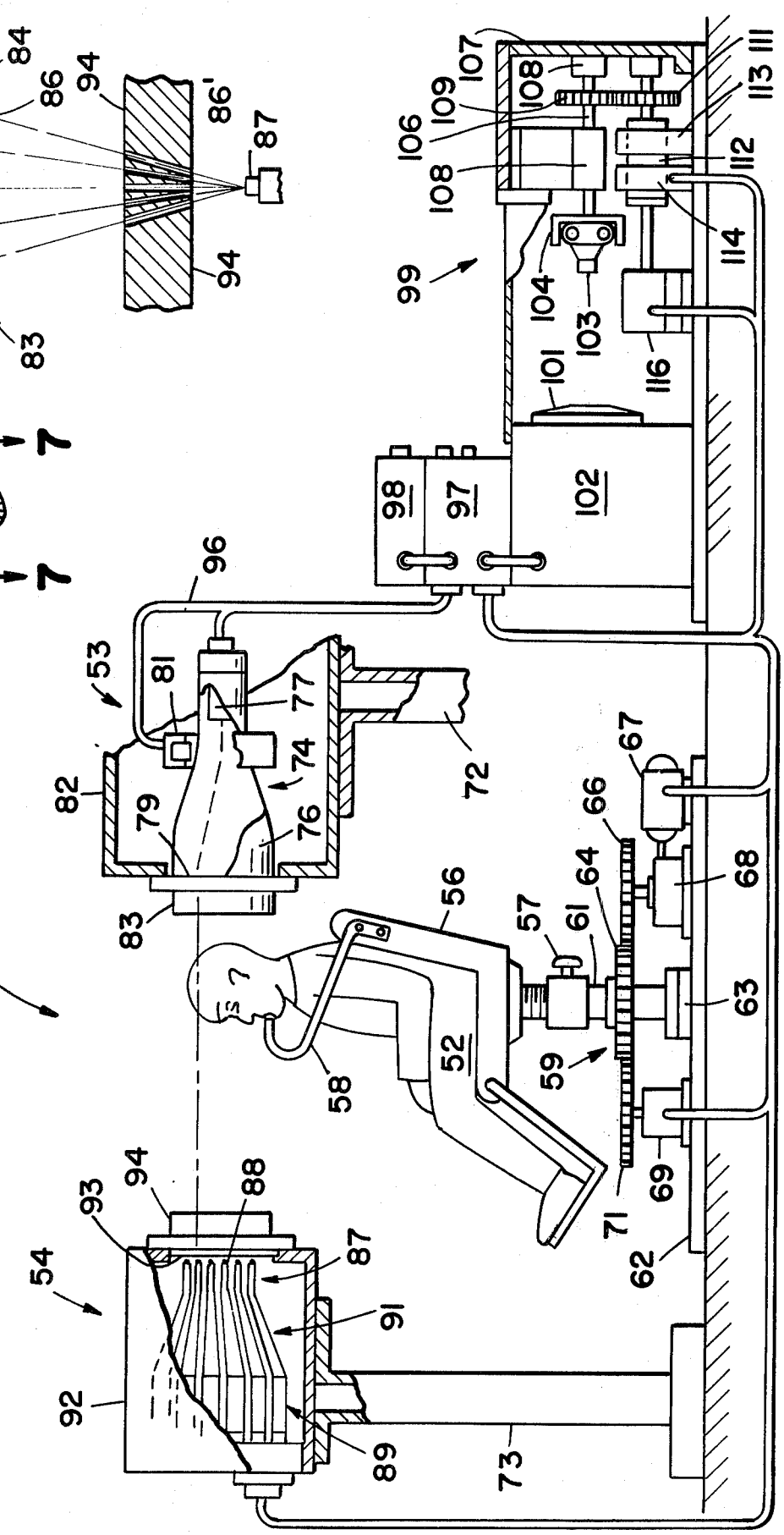

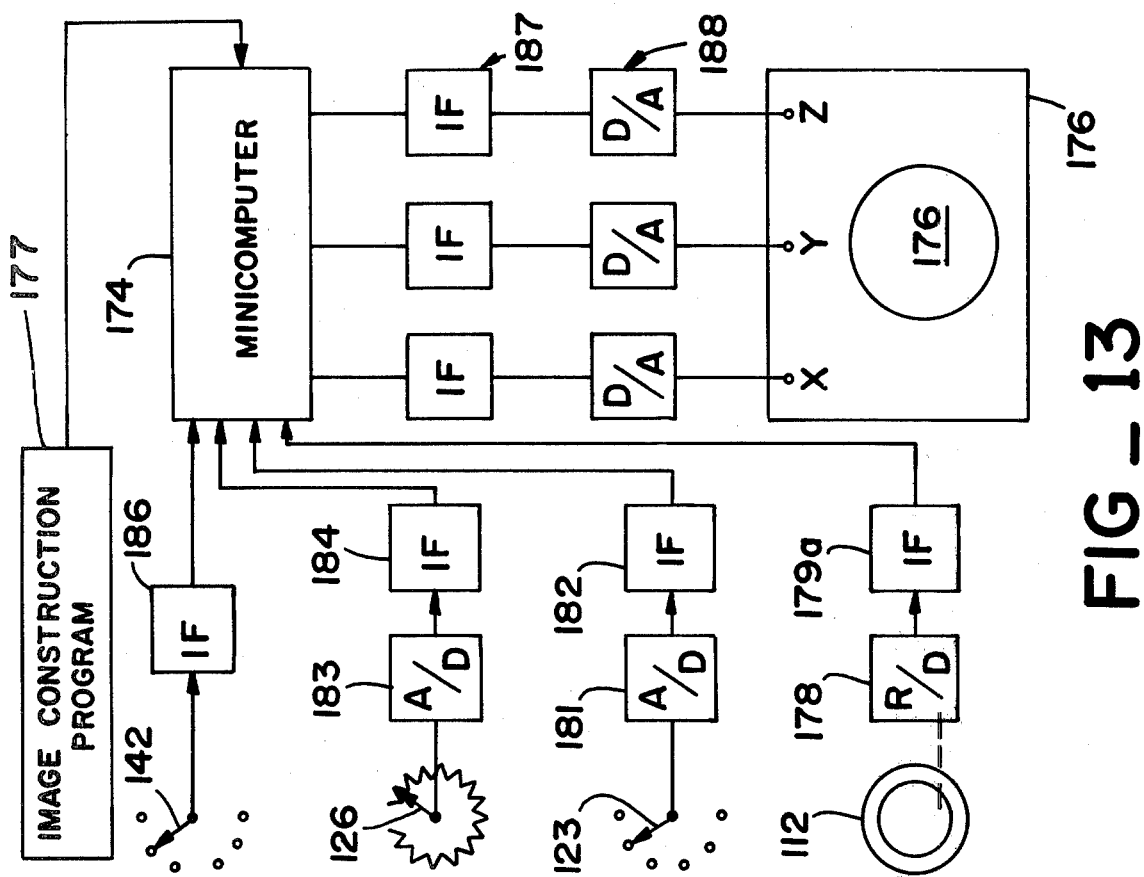
FIG_13
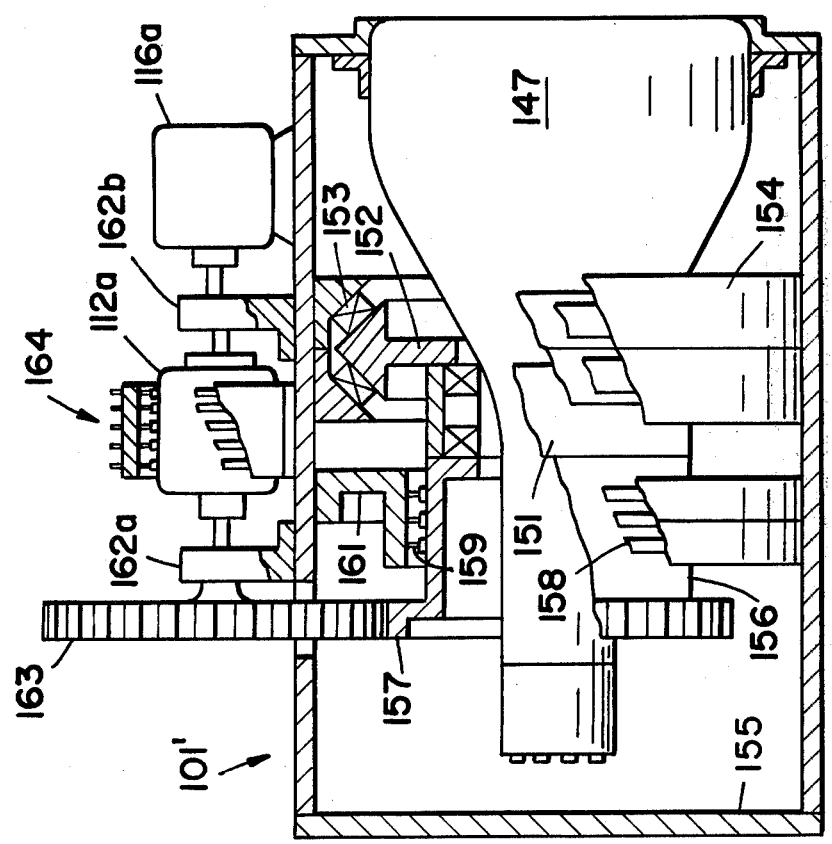
FIG_8

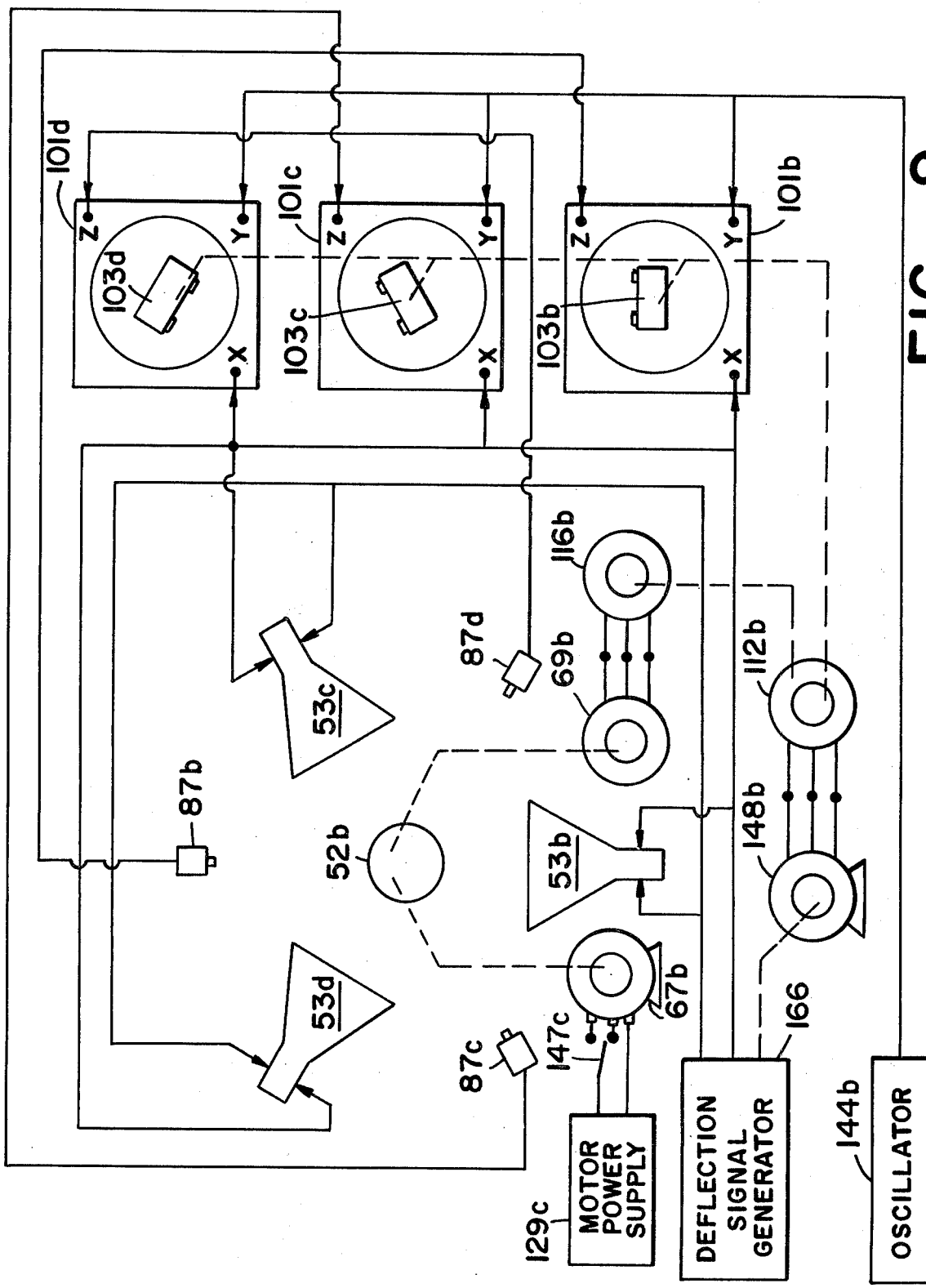
FIG_9

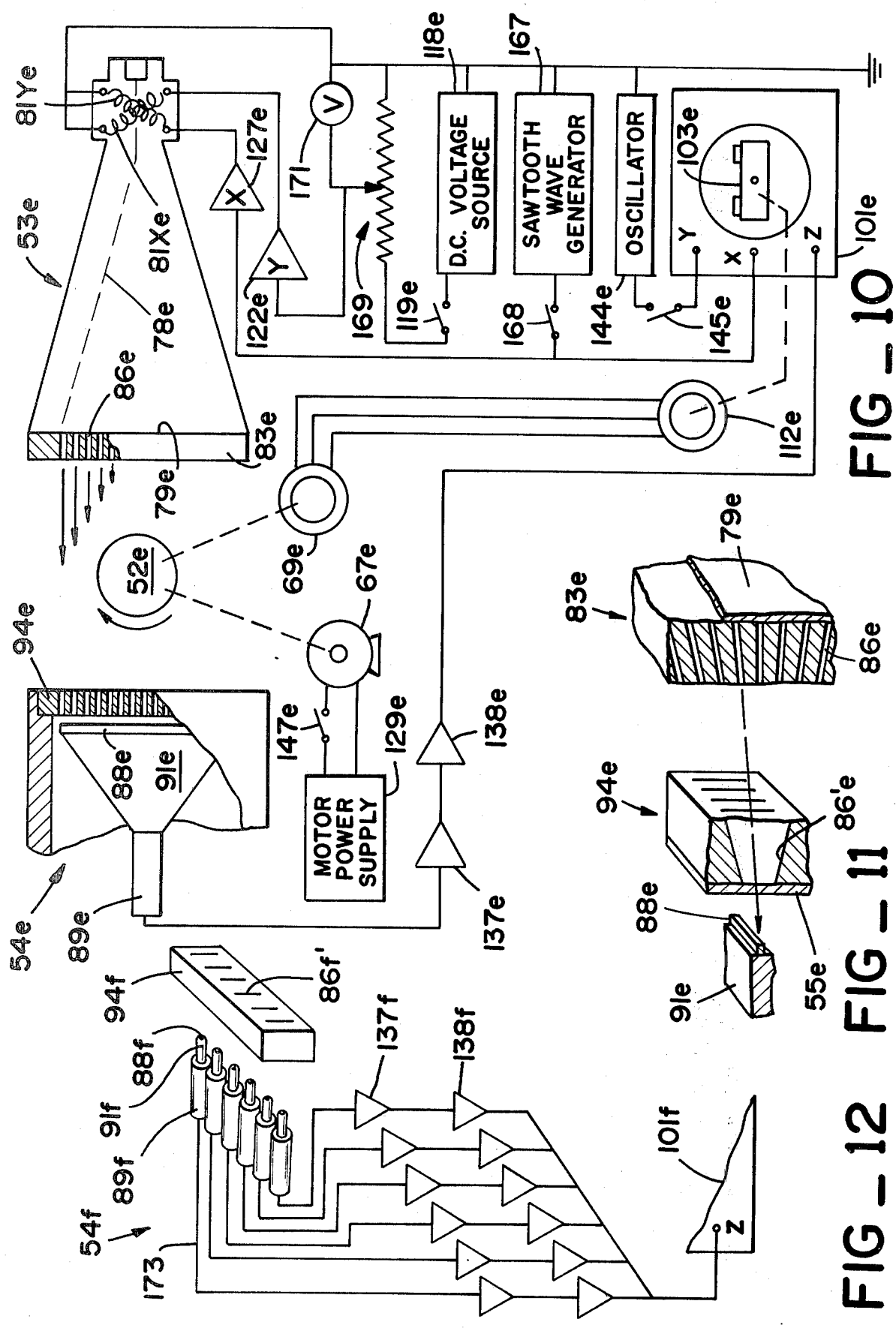

TOMOGRAPHIC X-RAY SCANNING SYSTEM

BACKGROUND OF THE INVENTION

This invention relates to the production of tomographic X-ray images and more particularly to methods and apparatus for generating data from which visible images may be derived that display a cross-sectional or oblique sectional radiographic view of a subject taken along one or more planes through the subject.

While the invention will be herein discussed primarily with reference to medical radiology for purposes of example, it should be understood that the method and apparatus are equally adaptable to the X-ray analysis of subjects other than medical patients or other living organisms. The invention is equally applicable to the inspection of metallurgical castings for internal flaws, for example, and to other usages in which the internal structure of an inanimate object is to be studied.

The conventional X-ray image of a subject as used for medical diagnostic purposes or the like has a serious disadvantage in that the visible image which is produced on a sheet of photographic film or on a fluorescent screen is not representative of a single sectional plane through the subject but instead contains overlapping or superimposed images of various organs, bones and other regions of differing X-ray transmissiveness which are distributed throughout the volume of the subject. Consequently, it is often difficult or impossible to obtain certain desired information from the image. Further, conventional radiology does not provide for views of a subject taken along planes parallel to the path of the X-rays through the subject.

In order to overcome these problems various tomographic techniques have heretofore been developed for obscuring data in the image that derives from regions of the subject located apart from a selected plane. One simple technique for accomplishing this result in conventional radiology is to move the X-ray source and the photographic film in opposite but parallel directions during exposure. Under this condition only one plane within the subject remains in sharp focus on the film. While this can be useful in many situations, one's ability to distinguish between data in the plane of interest from the blurred background image data is still considerably less than would be desirable. Further, the technique is limited insofar as variation of the orientation of the imaged plane is concerned.

To overcome these limitations of older procedures, much effort has recently been made to develop a new technique known as computed tomography. In most computed tomographic X-ray systems as heretofore constructed, a conventional point X-ray tube is situated on one side of the subject and a point X-ray detector on the other. The source and detector are then moved synchronously in parallel directions to perform a rectilinear scan across a plane transecting the subject. The output of the detector in the course of this scan is representative of variations of X-ray transmissiveness along a series of parallel zones through the subject which lie in the plane of the scan. This information is stored together with data indicative of the point in the scan at which each unit of such information was generated. The source and detector are then rotated relative to the subject or the subject is rotated and a similar scan is then made at the changed angular position. Typically, the rotational repositioning is repeated a very large number of times with the rectilinear scan being repeated at each angular position. The stored X-ray count information and positional data are then utilized to generate a visible image of a cross-sectional plane through the subject in which areas of different X-ray transmissiveness are clearly defined and readily distinguishable. A variety of techniques for generating the desired cross-sectional planar X-ray image from the stored data are known. These are primarily variations of a technique known as the summation or back projection method which is described for example in the journal RADIOLOGY 87; 278 (1966) in an article by Kuhl and Edwards. Although analog systems have been devised, most of the recently developed tomographic systems of this general kind utilize a digital computer to perform much of the operations required for image generation from the X-ray detector output information and scan position data, such a system also being described in the journal RADIOLOGY 91; 975 (1968) by the same authors.

These improvements in X-ray cross-sectional imaging by computed tomography have proved to be extremely useful in medical radiology, particularly for distinguishing between biological tissues of only slightly varying densities such as occur in the brain, abdomen and chest cavity. The recent development of a computed tomographic brain scanner in particular had led to extreme medical interest in the further possible capabilities of X-ray tomography as a powerful diagnostic tool.

The computed tomographic systems presently known to the art tend to be extremely complex and costly. Size, space and power requirements further limit the availability of such systems to a few large, well financed medical centers. Much of the cost, complexity and size of this apparatus derives from the need to provide precision mechanisms to effect the controlled repetitive rectilinear scanning motion alternated with precise angular repositioning motions of the source and detector structure relative to the subject to be analyzed. Further, because the scanning is accomplished mechanically, undesirably long periods are required to produce a tomographic image. If sectional X-ray images are to be produced for more than one plane through the subject, or for oblique planes, the mechanical positioning and scanning structure becomes even more complex.

SUMMARY OF THE INVENTION

This invention provides a method and apparatus for producing computed tomographic X-ray images more economically, more rapidly and with less massive and complex apparatus.

Instead of the conventional point source of X-rays, the invention includes a scanning X-ray source in which an electron beam is repetitively swept across a broad target anode plate to produce a moving point source of X-rays and to thereby accomplish the scanning action electronically rather than mechanically. Accordingly, in the simplest form, provisions for physical movement of the X-ray source and detector structure relative to the subject may, if desired, be limited to a relatively uncomplicated rotational positioning means although certain additional positioning structures, relatively simple in comparison with prior systems, may be present for special purposes. Further, provisions may be made for obtaining image data for a series of parallel planes or for oblique planes from a single sequence of scans. The X-ray detector output data may be stored and processed to produce a visible X-ray tomograph either by conventional digital computer techniques or by an advantageous analog system wherein the X-ray detector output signals produce a display on a cathode ray tube that is recorded and intrinsically processed by a camera viewing the face of the cathode ray tube during the scanning procedure. Relative rotation between the camera and the cathode ray tube display during the scanning process results in the desired tomographic image when the film from the camera is developed.

Accordingly, it is an object of this invention to provide for the production of tomographic X-ray images more economically and with the use of less complex and less costly apparatus.

It is another object of the invention to provide for the production of such image data in a more rapid manner.

It is still another object of the invention to provide for the production of tomographic image data for a plurality of different planes through a subject, which planes may be cross-sectional or may be inclined, from a single X-ray scanning sequence of a subject.

The invention, together with further objects and advantages thereof, will best be understood by reference to the following description of preferred embodiments taken in conjunction with the accompanying drawings.

BRIEF DESCRIPTION OF THE DRAWINGS

In the accompanying drawings:

FIGS. 3A and 3B are diagrammatic depictions which facilitate an understanding of how the X-ray detector output and positional data of the systems shown in FIG. 1 or 2 may be utilized in a back projection technique to generate a cross sectional tomographic X-ray image of a plane transecting a subject, FIG. 3C is a diagrammatic view illustrating a procedure for refining the visible image produced by the back projection technique and FIG. 3D depicts an optical filter used in the procedure of FIG. 3C, FIG. 4 is an elevational view of mechanical aspects of a first embodiment of a system for producing tomographic X-ray images of cross sectional or oblique planes through a medical patient, certain portions of the apparatus being shown broken out to illustrate internal detail, FIG. 6 is an elevation view of a portion of an X-ray collimator which may be employed in the system of FIG. 4 to reduce radiation dosage to a medical patient, FIG. 7 is an enlarged sectional view taken along line 7—7 of FIG. 6 further illustrating a suitable construction for the collimator, FIG. 8 is a broken-out elevation view illustrating a modified form of analog data processing system for generating a visible image from the data produced by the X-ray scanning system of FIGS. 4 and 5, FIG. 9 illustrates a modified form of the X-ray tomographic system which employs a plurality of X-ray sources, FIG. 10 depicts still another variation of the system providing for a rectilinear scanning geometry, FIG. 11 is an enlarged fragmentary perspective view of certain portions of the X-ray source, X-ray detector and collimator structures of the system of FIG. 10, FIG. 12 illustrates a modification of the X-ray detector of the system of FIG. 10, and FIG. 13 is a diagram illustrating the use of a digital computer to perform certain data processing functions which are accomplished by analog means in the previously depicted systems.

DESCRIPTION OF THE PREFERRED EMBODIMENTS

Figure 1:
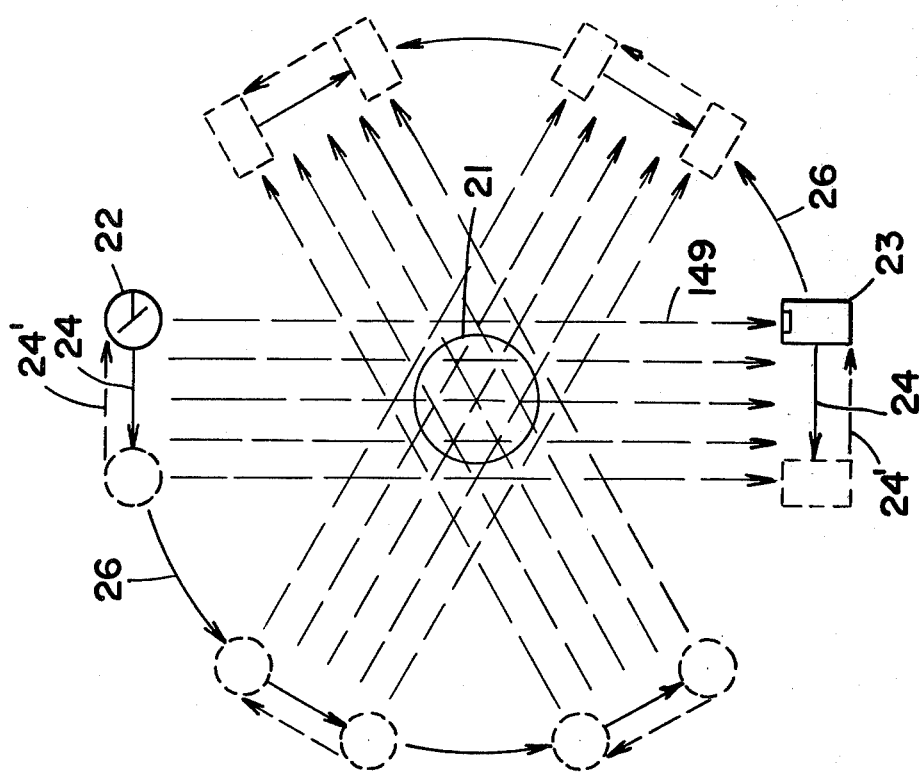
FIG. 1 is a diagrammatic depiction, for purposes of background and comparison, of certain basic positioning and scanning motions required to produce a computed tomographic cross-sectional X-ray image of a subject using conventional apparatus and techniques.

An understanding of specific representative embodiments of the present invention is facilitated by first briefly reviewing the steps and procedures involved in producing a conventional computed X-ray tomograph taken along a plane transecting a subject. Referring now to FIG. 1, the conventional system as designed, for example, for scanning a subject 21, which may be the head of a medical patient for example, involves situating the subject between a conventional point source X-ray tube 22 and an X-ray detector 23 of the kind having a small radiation-sensitive area and which produces electrical output pulses in response to X-rays impinging on the sensitive area. During a first stage of the scanning process, the source 22 and detector 23 are synchronously moved in parallel linear directions as indicated by arrows 24 to complete an initial scan of the subject. During this initial rectilinear scan the output signals from detector 23 together with signals indicative of the instantaneous position of the detector are stored in a computer or by other means. A single scan of this kind contains information on the X-ray transmissiveness of a series of parallel zones within a cross sectional plane transecting the subject 21 but taken by itself this information from a single rectilinear scan does not provide a basis for generating a very meaningful cross sectional image. To obtain the additional data needed for this purpose, the source 22 and detector 23 are restored to the initial positions as indicated by arrows 24' and jointly rotated about an axis normal to the plane being scanned as indicated by arrows 26 in FIG. 1. Another rectilinear scan is then effected by simultaneously moving the source and detector in parallel directions and the output signal of the detector and signals indicative of source and detector position along the second scan are again recorded. The source and detector may then again be restored and then rotated further and still another rectilinear scanning operation and storing of detector output and position signals is effected. While only three rectilinear scanning steps, interrupted by rotations of 60 degrees, are shown in FIG. 1 for clarity of illustration, in practice a much larger number of rectilinear scans are usually performed with the rotational movement of the source and detector between successive scans being as little as one degree of arc.

If data for more than one plane transecting the subject 21 is to be obtained using the conventional apparatus of FIG. 1, either the source and detector structure or the subject 21 must be moved in a direction perpendicular to the plane of FIG. 1 and then the repetitive scanning and rotational process must be repeated for each such plane. If the plane through the subject 21 which is to be imaged is an oblique one, rather than a strict cross section, it may be seen that either the source and detector structure or alternately the subject 21 must be tilted relative to the other and the entire process repeated.

As is apparent from the foregoing, the mechanical mechanisms needed to position the subject 21 and the source and detector structure in such a way as to enable the rectilinear scanning motions and the angular motions must of necessity be bulky and complex. Cost and complication are even greater where motion of the subject or, alternately, the source-detector structure in a direction normal to the plane of FIG. 1 is provided for in order to obtain information for constructing images of a series of parallel planes. The support and drive structure becomes still more complex if imaging of oblique planes through the subject is to be provided for by controlled tilting of either the subject or the source and detector.

Figure 2:
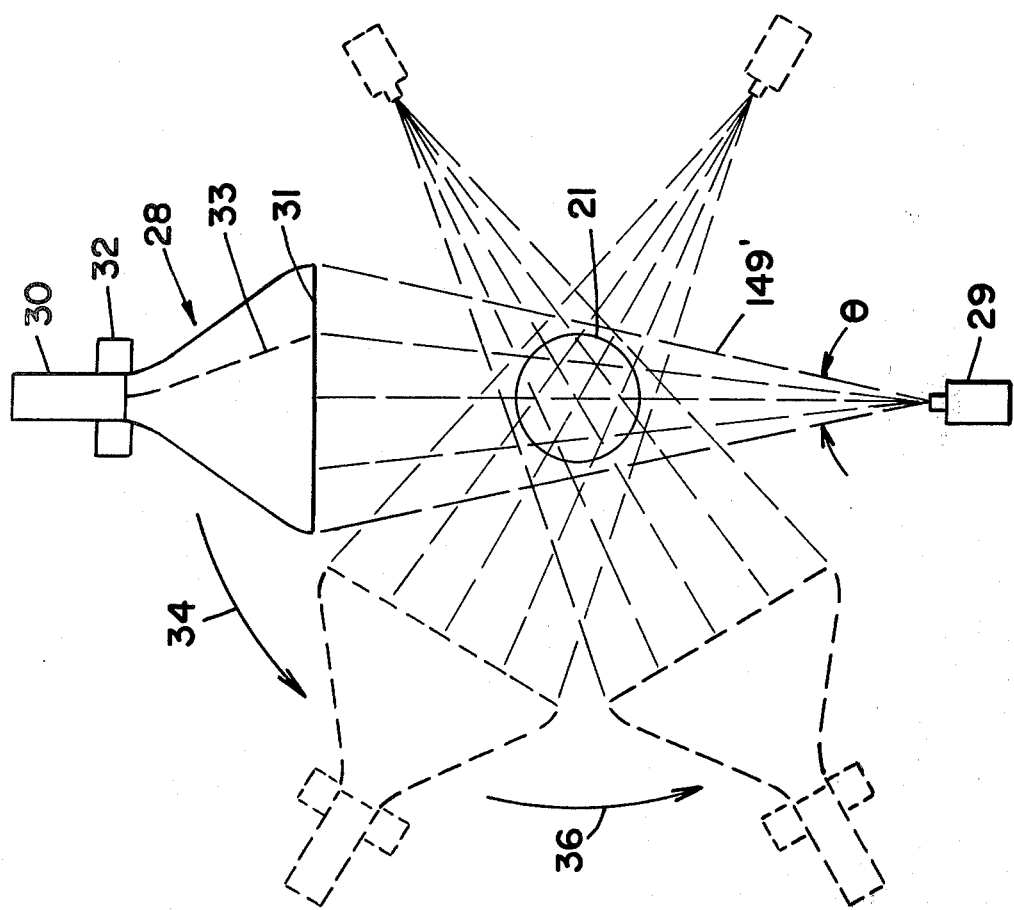
FIG. 2 is a diagrammatic depiction of certain basic steps utilized to produce a computed tomographic X-ray image of a cross sectional plan through a subject by means of the present invention.

Positioning and drive structure for such purposes is greatly simplified and reduced by the present invention, certain basic principles of which are depicted diagrammatically in FIG. 2. In the present invention as shown in FIG. 2, the subject 21 is again positioned between an X-ray source 28 and an X-ray detector 29. Dectector 29 may be essentially similar to that employed in the system of FIG. 1 in that it is of the form having a very small effective radiation-sensitive area and produces an electrical signal indicative of X-rays impinging on that area. However, the X-ray source 28 of FIG. 2 differs from that previously described in that it is of the scanning form which has an electron beam gun 30 at a cathode end and a broad target-anode end surface 31 against which the electron beam impacts to produce X-rays. Source 28 also has beam deflector means 32 for sweeping electron beam 33 across the broad target end to produce a moving point X-ray source. Thus the repetitive scanning operations required in the tomographic process are accomplished electronically rather than by mechanical means and the structure as a whole may be greatly simplified. In particular, with the source 28 and detector 29 at an initial position, the electron beam 33 is swept across target plate 31 to effect the first scan. During this period, the output signals from the detector 29 are stored as are the deflection signals at deflection means 32 which are indicative of the instantaneous position of the scan. Source 28 and detector 29 may then be rotated about an axis normal to the plane along which the subject is being scanned as indicated by arrow 34 in FIG. 2. The electronic scanning process is then repeated, after which the source and detector may again be rotated to a new angular position as shown by arrow 36 and the scanning process is again repeated. As in the case of the conventional system of FIG. 1, only three scans at three angular positions have been depicted in FIG. 2 for clarity of illustration but in most cases, in order to obtain a more accurate image, a much larger number of scans are made at smaller angular intervals.

The process described above with reference to FIG. 2 brings about a substantial reduction in size, mechanical complexity and cost of the system relative to the conventional practice of FIG. 1 by accomplishing the scanning action electronically. In most cases, it is only necessary to provide simple rotational mechanical structure for effecting the angular movement of the source 28 and detector 29 structure between successive scans or, alternately, to simply provide for controlled rotational motion of the subject 21 between scans. Rotational means of this kind may be much less complex mechanically than the structure required for the conventional system. Further, the electronic scanning action realized in source 28 can be accomplished more rapidly than can mechanical movement of the source and detector for such purposes. Still further, as will be hereinafter described in more detail, a series of detectors 29 can be disposed along a line normal to the plane of FIG. 2 to enable the generation of data for a series of parallel planes or for one or more selected oblique planes during a single sequence of scans of the subject 21, no mechanical mechanisms for repositioning either the source-detector combinations or the subject being necessarily required for such purposes. It is in fact possible to construct an embodiment of the system of FIG. 2 in which no mechanical movement of either the source-detector or the subject is required at all. This may be accomplished by providing a plurality of scanning sources 28 and detectors 29 distributed angularly around the subject 21 to perform the desired scans from different angular positions. However, in most cases the added cost and complexity of the additional scanning X-ray sources is such that it is more feasible to use a single source and simple rotational positioning means as has been illustrated and described with respect to FIG. 2.

It may also facilitate understanding of the detailed specific examples of the invention to briefly review the basic principles by which a cross sectional tomographic image of a scanned subject may be constructed from the information obtained by the scanning procedures of either FIG. 1 or 2. Principles of the back projection technique may be understood by referring to FIGS. 3A and 3B. To avoid excessive complexity in FIG. 3A the subject 21 to be scanned is represented by a sphere 37 formed of a relatively X-ray transmissive material such as aluminum having embedded therein, at an off-center position, a smaller sphere 38 of relatively dense material such as lead. It may be seen that the X-ray count information and scan position information from a first scan made in the direction designated by arrow 39a in FIG. 3A can, if desired, be used to produce a film transparency 41a which stores the information and data in optical form. In such a transparency 41a the light-transmissiveness of successive zones along the film is proportional to the X-ray count from the detector at each successive point in the scan. Thus, the transparency 41a in the present example would exhibit side regions 43a of uniform high optical transparency at the beginning and end portions of the scan, where X-rays did not pass through the sphere 37 at all, but at the region where the scan passed through the small dense sphere 38 a dark, relatively opaque narrow band 44a appears. At each side of band 44a, bands 46a of intermediate light-transmissiveness appear where the X-ray scan passed through the larger sphere 37 but not through the dense sphere 38.

A similar transparency 41b may be prepared for a subsequent scan at a rotated angular position as previously described. It should be observed that the position of the bands 43b, 44b and 46b appear shifted and are inclined at different angles on this second transparency 43b. Similarly, still another such transparency 41c may be prepared after the source and detector have again been turned angularly to scan at still another angle. Again, the resultant bands 43c, 44c and 46c of differing light-transmissiveness are shifted in position and inclined at a still different angle.

Referring now to FIG. 3B, the desired cross sectional tomographic X-ray image may be produced by overlaying the three transparencies 41a, 41b and 40c with the centers of all three being coincident while maintaining the angular orientation of the three transparencies similar to that depicted in FIG. 3A. As shown in FIG. 3B, the result is that the various bands on the overlaid transparencies intersect to define an image of the approximate outline of spheres 37 and 38 seen in cross section. For example, in FIG. 3B, the region 38' of intersection of all three bands 44a, 44b and 44c constitutes a relative opaque area at the position of the small dense sphere 38 in the desired cross section. Similarly, the broader region 37' of intersection of bands 43 and 46 form an area of intermediate light-transmissiveness constituting an approximate outline of the larger sphere 37.

If a broad light source is viewed through the overlaid transparencies of FIG. 3B, it may be seen that an approximation of the desired cross section is visible but that it is less than ideal for two reasons. First, spurious background detail is present in that the various bands 43, 44 and 46 are visible to some extent outside the regions of the images 38' and 37' of the spheres. Second, the outlines of the large sphere image 37' and the small denser sphere image 38' are not circular as would be the case in a precise cross section but are polygonal and are accompanied by star-like points around the periphery of somewhat lessened opacity. Instead of being circular, the sphere images 37' and 38' appear to resemble six-pointed stars in this example. It is for this reason that the scanning process is repeated many more times than has been represented in FIGS. 3A and 3B with the angular difference between each such scan being much smaller than depicted. To the extent that the number of scans is increased and the angular amount of the change between successive scans is decreased, the two effects described above are diminished. Starlike points diminish in size and intensity and the images 37' and 38' of the spheres become progressively closer to circularity. Visibility of those portions of the bands 43, 44 and 46 outside the region of the sphere images in the cross section is blurred and reduced by the repetitive scanning at small angular increments.

If scanning has been performed from enough closely spaced angles, the image produced by the above described technique may be sufficiently close to a true cross section to be usuable for certain purposes. Where this is not the case, known procedures for further refining the image may be utilized. One such technique is described in a publication by Bates and Peters, New Zealand Journal of Science 14:883(1971) specifically in FIG. 8 of that publication and in the portion of the text beginning on page 894. In that technique, as shown in FIG. 3C of the present application, the transparencies 41 overlayed as described above are disposed normal to the optical axis of a first double convex lens 45a and at one focal length therefrom, points 50 being the focal points of the lenses depicted in FIG. 3C. An optical filter 55 is disposed slightly less than one focal length from the other side of lens 45a and as shown in FIG. 3D is of the form having an optical transmissiveness which is proportional to radius. In other words areas of the filter are progressively less opaque in proportion to distance from the center. Referring again to FIG. 3C, a second double convex lens 45b is situated one focal length away from the closest focal point of lens 45a and a sheet 55 of unexposed photographic film is disposed slightly less than one focal length away from lens 45b. A beam of coherent light from a laser 60 is then momentarily directed through transparencies 41 along the optical axis defined by the lenses 45. The refined image is produced by subsequent development of the film 55.

It should be understood that the above description of how a cross sectional X-ray image of a subject may be constructed from X-ray detector output information and scan position data is intended only to provide for understanding that the information needed for such an operation is in fact contained within the X-ray detector signals and position signals. The above description is illustrative of basic principles of the back projection technique rather than necessarily representing steps which must be used in the practice of the present invention. As a practical matter, output information from the X-ray detector and scan position data is often digitized, in conventional X-ray tomograph systems, and supplied to a digital computer. The computer performs mathematical operations analogous to the procedure described above and then controls a cathode ray tube display at which the cross sectional image is presented visually or for recording by a camera. The present invention is adaptable to such computer-controlled image construction and display as will hereinafter be described in more detail. However, the present invention may also utilize an analog form of data processing system in which the desired visible cross sectional image is produced by a system which includes a cathode ray tube display and camera which undergo relative rotation in the course of the scanning operations as will hereinafter be described in more detail.

Considering now a specific example of the invention in more detail, reference should be made initially to FIG. 4. Although it may be adapted for many other purposes, the system 51 of FIG. 4 is primarily designed for scanning the brain region of a medical patient or subject 52 to obtain tomographic X-ray images displaying variations of X-ray transmissiveness at different areas of one or more cross-sectional planes through the patient's head or of inclined planes through the head. Basic components of the system include a scanning X-ray source 53 directed towards an X-ray detector assembly 54. Means for supporting the subject 52 between the X-ray source and X-ray detector assembly in this example is a chair 56 positioned to locate the subject's head between the source and detector assembly. Chair 56 may have an extendable and contractable support means 57 to accommodate to subjects of different size. To aid the subject in remaining immobile during the scanning operations, a brace 58 may extend from the chain to the position of the subject's mouth so that it may be clenched in the subject's teeth, the brace 58 being preferably formed of a material of high X-ray transmissiveness such as certain known plastics.

In accordance with the principles hereinbefore described, either the X-ray source 53 and detector assembly 54 must be rotatable as a unit about a vertical axis through the plane to be imaged or else the patients 52 themselves must be rotatable in a precisely controlled manner. In the present example this relative angular motion is provided by rotational positioning means 59 which turn chair 56 about the vertical axis defined by the supporting post 61 of the chair. For this purpose post 61 is coupled to a base platform 62 through a bearing 63 and a gear 64 is secured to the post in coaxial relationship thereon. A drive gear 66 engages gear 64 and is coupled to a D.C. electrical drive motor 67 through a reduction gear assembly 68. Drive motor 67 is energized and controlled by means to be hereinafter described. To produce an angular position signal indicative of the angular relationship of the subject 52 relative to the X-ray source and detector, at any given time, a transmitter synchro 69 is mounted on platform 62 with the rotor shaft of the synchro being coupled to gear 64 through another gear 71 of equal diameter.

As the angular motion is provided for in this example by turning of the subject 52, the X-ray source assembly 53 and X-ray detector assembly 54 may both be mounted upon fixed support structures 72 and 73 respectively.

The X-ray source assembly 53 contains a scanning X-ray source 74 which may be of the form described in my copending application Ser. No. 481,954, filed June 24, 1974 and entitled X-RAY SCANNING METHOD AND APPARATUS (now U.S. Pat. No. 3,949,229). Basic elements of such an X-ray source include a vacuum envelope 76 containing an electron gun 77 at the cathode end. Electron gun 77 emits an electron beam 78 towards a broad target anode plate 79 at the opposite end of the vacuum envelope whereby X-rays are generated at the point of impact of the electron beam. An annular electron beam deflection yoke 81 encircles an intermediate portion of the vacuum envelope 76 and may be of known magnetic deflection type or electrostatic deflection means may be used, a magnetic deflection yoke being utilized in this particular example. Deflection yoke 81 enables controlled deflection of the electron beam 78 within the vacuum envelope to sweep the electron beam back and forth across a predetermined path on the target anode plate 79 to produce a moving point source of X-ray. This predetermined scan sweep path will be identified as the X scan and extends horizontally in this example. This X scanning action is controlled by X deflection signals supplied to the yoke 81 as will hereinafter be discussed in more detail. Y deflection signals may also be applied to the yoke 81 to select the vertical level of the predetermined path of electron impact across target anode plate 79 to enable tomographic X-ray images to be made of cross sections through the subject's head taken at different levels.

To absorb X-rays which are emitted from the target plate 79 in directions other than that of the X-ray detector assembly 54, the scanning X-ray source 74 may be enclosed in a housing 82 formed of thick X-ray-absorbent material such as lead for example. Although it is not essential from the standpoint of producing the desired tomographic sectional X-ray image and may be dispensed with in some circumstances such as where inanimate subjects are being examined, unnecessary exposure of the subject 52 to radiation may be reduced by situating an X-ray focusing collimator 83 between the X-ray source and the subject, preferably at the face of the X-ray source assembly to form a continuation of the housing 53. As may be seen by reference to FIGS. 6 and 7 in conjunction with FIG. 4, the collimator 83 may be basically of the known construction employed in conventional radiography wherein a thick radiation-absorbent body 84 formed of lead or other dense material is provided with a large number of minute spaced-apart passages 86 through which X-rays are transmitted toward the X-ray detector 87 while X-rays traveling in other directions are absorbed. The passages 86 are preferably convergent towards the position of the detector 87. To provide for the production of tomographic X-ray images taken along oblique planes as opposed to strictly horizontal planes, the passages 86 of the collimator 83 may be formed to have a greater depth than width as best seen in FIG. 6. For clarity of illustration, the passages 86 are shown in FIG. 6 as being larger in size and fewer in number than is typically the case. Collimating grids of this general type are often manufactured with as many as 100 such passages per linear inch. To supress grid line artifacts in the X-ray images, collimator 83 and other collimators to be hereinafter described may be of the Bucky type, if desired, which are oscillated in a plane normal to the X-ray flux.

Referring again to FIG. 4, the X-ray detector assembly 54 in this example contains a column of vertically spaced-apart radiation detectors 87 each formed by a very small scintillation crystal 88 of form which produces visible light in response to X-rays. Other known forms of X-ray detector, such as ionization chambers, proportional counters, solid state detectors or the like, may also be used provided that the active radiation-sensitive areas of each individual detector is minute in relation to the breadth of the target anode plate 79 of the X-ray source. To provide for increased resolution in the X-ray tomograph images, the radiation-sensitive areas of detectors 88 are preferably minimized to the extent possible within the need to obtain an adequately high count rate from the radiation flux which can be tolerated by the subject 52. As scintillation detectors are used in this example, each scintillation crystal 88 is coupled to an associated individual one of six photomultiplier tubes 89 by an associated individual one of six light pipes 91 so that a scintillation of visible light produced by an X-ray impinging on a crystal is transmitted to the associated phototube 89 to produce electrical output pulses as will hereinafter be discussed in more detail. The use of six X-ray detectors in this embodiment is for purposes of example only and enables cross-sectional planes through the head of the subject 52 to be imaged at any of six different levels during the scanning procedure and also enables data for oblique sectional images for any of thirty-six different planes through the subject's head to be generated from the information obtained during a single scanning procedure. It should be understood that if information from only a single plane is desired from a single scanning procedure, then only a single one of the X-ray detectors 87 need be present. Similarly, if information for a larger number of planes is desired from a single scanning procedure, a larger number of the X-ray detectors may be included in assembly 54.

To shield scintillators 88 from ambient X-rays originating from points other than the scanning X-ray source 53 and also to shield the scintillators 88, light pipes 91 and photomultiplier tubes 89 from ambient visible light, such elements may be enclosed within a thick radiation-absorbent opaque housing 92 formed of a material such as lead. The portion of housing 92 situated between the scintillation crystals 88 and the subject 52 is defined by a thin plate 93 which is also opaque to visible light but, unlike the remainder of the housing, is relatively transmissive to X-rays, a thin aluminum sheet being one material suitable for this purpose. Spurious information in the X-ray tomograph images may be further reduced by providing another lead collimator 94 at the face of the detector assembly 54 adjacent plate 93 to absorb X-rays, such as secondary X-rays, that do not originate at the target anode plate 79 of the X-ray source assembly 53. Such a collimator 94 may be basically similar to the previously described source collimator 83 except that as illustrated in FIG. 7 the X-ray-transmissive passages 86' of collimator 94 may be limited to a smaller region of collimator 94 since the X-rays which are of interest converge towards the X-ray detectors 87.

Referring again to FIG. 4, the scanning X-ray source 74, the photomultiplier tubes 89 of X-ray detector assembly 54, the chain drive motor 67 and position signal synchro 69 are all electrically coupled through suitable multi-conductor cables 96 with an electronic control circuit housing 97 having an adjacent electrical power supply housing 98, the electrical circuit of the system being hereinafter described. Although the electronic signals developed by the above-described devices may be digitized and processed by a digital computer in the known manner to produce the desired computed tomographic X-ray images, this particular example of the invention uses an analog data processing system 99 for this purpose.

Mechanical aspects of the analog data processing system 99 may include a cathode ray tube oscilloscope 101 preferably mounted in a housing 102 adjacent electronic console 97, the oscilloscope being of the known form which generates a visible display at the face of the tube as determined by horizontal or X-axis deflection signals, vertical or Y-axis deflection signals and Z-axis intensity signals applied to terminals of the oscilloscope.

To record and further process data displayed on the face of oscilloscope 101, a camera 103 is positioned in front of the oscilloscope to view the visual display and to record on film the information which is displayed visually on the face of the tube. For purposes which will hereinafter be described, relative rotation between the camera 103 and the visible display on oscilloscope 101 occurs during the scanning procedure and for this purpose the camera 103 may be supported by a bracket 104 attached to a shaft 106 that is rotatably journaled to support structure 107 by suitable bearings 108.

For reasons to be hereinafter explained in connection with the operation of the system, camera 103 is rotated when the subject 52 is rotated by drive motor 67 and the camera also rotates as the electron beams of the X-ray source and oscilloscope undergo each horizontal or X-axis scanning movement. To provide for these motions, a gear 109 on camera shaft 106 engages an equal-diameter gear 111 mounted on the output shaft of a receiver synchro 112 which is electrically coupled to the transmitter synchro 69 of the patient's chair 56. The entire receiver synchro 112 is itself rotatable and accordingly is supported through a bearing 113 and provided with a slip ring and brush assembly 114 through which the necessary electrical connections may be made to the receiver synchro. To provide for the rotation of receiver synchro 112, it is disposed in coaxial relationship with another receiver synchro 116 and secured to the rotor shaft of synchro 116.

Figure 5:
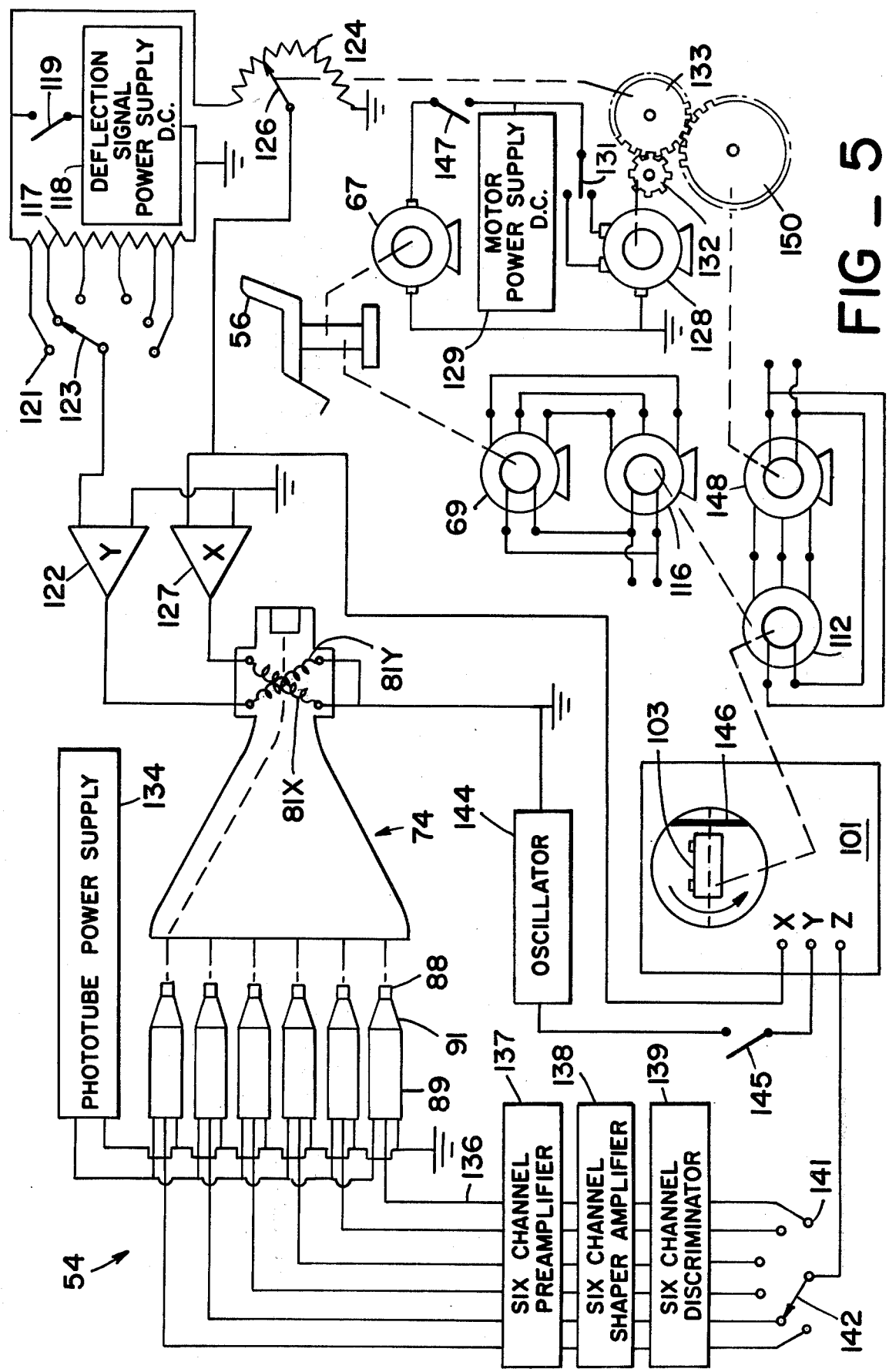
FIG. 5 is an electrical circuit diagram of the system depicted in FIG. 4.

Considering now the electrical circuit of the system 51, reference should be made to FIG. 5. Y-axis or vertical deflection signal voltage for controlling the vertical level of the electron beam sweep within scanning X-ray source 74 is derived from a resistor 117 connected across the terminals of a regulated D.C. power supply 118 through an on-off switch 119, one terminal of the power supply and one end of the resistor being connected to circuit ground. Six voltage taps 121 connect with resistor 117 at intervals therealong to enable any selected one of six voltage levels to be supplied to the inverting input of a Y deflection signal amplifier 122 through a six-position switch 123. The output of Y deflection signal amplifier 122 is connected to ground through the Y deflection coil 81Y of the X-ray source. Thus the vertical level of the point of impact of the electron beam of the scanning X-ray source 74 may be selectively adjusted by operating switch 123.

The variable X-axis deflection voltage for the scanning X-ray source 74 may be produced at a semi-circular resistor 124 also connected across power supply 118 through on-off switch 119. A pivoting wiper 126 is electrically connected to the input of an X deflection signal amplifier 127 which has an output connected to ground through the X deflection coil 81X of the scanning X-ray source. Thus, if wiper 126 is turned within circular resistor 124, an X or horizontal beam deflection voltage is applied to the X-ray source which voltage progressively rises from circuit ground to a maximum value. Reversal of the direction of wiper 126 motion then returns the voltage to the minimum value to effect the desired horizontal scanning action of the X-ray source as previously described. To turn wiper 126 for this purpose, reversible D.C. drive motor 128 may be connected across a motor power supply 129 through a directional control switch 131. Motor 128 turns a small-diameter gear 132 which engages a larger-diameter reduction gear 133 that is mechanically coupled to wiper 126 to rotate the wiper when switch 131 is at either the forward drive or reverse drive positions.

Considering now circuits associated with the X-ray detector assembly 54, the six phototubes 89 which respond to light pulses originating from the X-rays impinging on scintillation crystals 88 are coupled to a conventional photomultiplier tube power supply 134 and each phototube has an individual output pulse conductor 136. Conductors 136 connect with individual inputs of a six-channel preamplifier 137 which has outputs connected to a six-channel pulse shaper amplifier 138 and which in turn has outputs connected to the six inputs of a six-channel pulse discriminator 139 which suppresses relatively low magnitude pulses such as may arise from detector and circuit noise or other spurious sources. The preamplifier 137, shaper amplifier 138 and discriminator 139 may all be of the known contructions customarily employed in conjunction with photomultiplier tubes.

Output signals from discriminator 139 may be digitized and then processed by a computer to produce the desired tomograph. However, when the analog data processing system of this embodiment is used to construct the image, the six outputs of discriminator 139 are each connected to an individual one of six fixed contacts 141 of a multiple position switch 142. The movable contact of switch 142 is electrically connected to the Z-axis or intensity control terminal of oscilloscope 101. If the tomograph images are to be taken only along horizontal planes through the subject, switch 142 is operated in correspondence with the X-ray source Y deflection signal voltage selector switch 123. Thus when the switch 123 is set to locate the horizontal electron beam sweep of scanning source 74 at the uppermost level, shaped and amplified X-ray count output pulses from the uppermost photomultiplier 89 are transmitted to the Z terminal of the oscilloscope through switch 142. If switch 123 is adjusted to lower the vertical level of the electron beam sweep within X-ray scanning source 74 by providing a reduced Y deflection signal thereto, output pulses from a correspondingly lower one of the photomultiplier tubes 89 are transmitted to the Z terminal of the oscilloscope after shaping and amplifying. Thus operation of the two switches 123 and 142 enables scanning of the subject at any of six spaced-apart horizontal planes through the subject. If switches 123 and 142 are not set at corresponding positions, then scanning along inclined planes through the subject may be accomplished. For example if switch 123 is set to supply one of the higher Y deflection signals to the scanning X-ray source while switch 132 is set to couple one of the lower of the photomultiplier tubes 89 to oscilloscope 101, data is obtained for an inclined sectional plane through the subject. Any desired one of the six settings of switch 123 may be combined with any one of the six settings of switch 142 to provide image data for planes through the subject located at various heights and inclinations.

Through the above-described circuits, an X-ray count originating at the one of the detectors 87 which has been selected at a particular time by setting of switch 142 momentarily activates the beam intensity controls of oscilloscope 101 to cause a visible point of light to appear on the screen thereof. The position of the point of light on the face of the oscilloscope screen is determined by the X and Y deflection voltages which are being applied to the oscilloscope at that instant. To create a visible display which can be recorded and integrated by the rotating camera 103 to produce the desired X-ray tomograph image, the X-axis or horizontal sweep deflection terminal of oscilloscope 101 is coupled to the same wiper 126 which supplies the X deflection signal to the scanning X-ray source 74. Thus the electron beam of oscilloscope 101 repetitively sweeps horizontally from one side of the screen to the other in synchronism with the horizontal scanning motion of the electron beam of the X-ray source. Thus when an X-ray count is detected during the course of a scan the electron beam of oscilloscope 101 will be gated on briefly to produce a visible point of light situated at a corresponding position in the horizontal scan which is occurring in the oscilloscope. Means are provided to convert this point display of light on the oscilloscope face into a vertical band of light analagous to the bands 44 and 46 of the transparencies 41 which were previously described with reference to FIG. 3A and FIG. 3B in connection with the back projection technique of image construction. For this purpose, the Y or vertical deflection signal terminal of oscilloscope 102 is connected to the output of an oscillator 144 which produces a bipolar output voltage having a frequency much higher than the horizontal scan frequency of the source and the oscilloscope. Thus the above-described point of light which would otherwise occur only along a central horizontal line across the face of the oscilloscope is spread out above and below that line. A visible vertical band 146 is thereby generated at the face of oscilloscope 102 and is recorded on the film within camera 103.

The visible vertical banding pattern of varying lightness and darkness produced on the face of oscilloscope 101 and recorded on film by camera 103 in the course of a single sweep of the electron beams of the X-ray source and the oscilloscope is essentially equivalent to a single one of the transparencies 41 of the back projection process of FIGS. 3A and 3B. As has been pointed out, additional such transparencies 41 must be produced, from additional scans taken with the subject at a different angular relationship to the X-ray source and detectors, so that the data recorded on the many transparencies may be combined in the manner previously described with reference to FIG. 3B to produce the desired tomograph. It is not essential that a separate film be used in the camera 103 for each scan taken at a different angular relationship nor that any separate film transparencies be literally overlaid with each other in the manner previously described with reference to FIG. 3B since a similar effect may be realized by simply multiply exposing a single film within the camera 103 during each of the individual scans of the scanning sequence provided that the camera 103 is rotated a corresponding angular amount each time that the patient 52 of FIG. 4 is rotated relative to the X-ray source and detector assembly between scans. The single film within camera 103 is, upon subsequent development, the practical equivalent of the overlaid transparencies depicted in FIG. 3B and provides the desired tomographic image.

The rotation of the camera 103 between scans for this purpose may be accomplished with shafts and gears but in this example is effected by the previously described synchro transmitter 69 which has stator terminals coupled to the stator terminals of the receiver synchro 116, the rotor terminals of the two synchros being coupled to a source of A.C. excitation in the known manner. Since receiver synchro 116 rotates the entire body of synchro 112, on which the camera 103 is supported, any angular motion of the patient's chair 56 is accompanied by a corresponding angular motion of the camera 103. The drive motor 67 for chair 56 may be coupled across the motor power supply 129 through a normally open control switch 147 and may be temporarily closed between scans to synchronously turn the patient and the camera by any selected amount.

Additional rotation of the camera 103, additive to that described above, is provided for by still another transmitter synchro 148 which has stator terminals coupled to the stator terminals of synchro 112, the rotor terminals of both synchros 148 and 112 being coupled to a common source of A.C. excitation current. This additive camera 103 rotation occurs in the course of each horizontal scanning sweep of the electron beams of the X-ray source and the oscilloscope and occurs since the rotor of transmitter synchro 148 is mechanically coupled to another gear 150 which engages the gear 133 that drives wiper 126 to produce the X deflection signal for the source and the oscilloscope. Gear 150 is of greater diameter than gear 133 so that the amount of rotation of the camera 103 is less than a complete revolution during the course of each scan. Considering now the purpose of this additional rotation of the camera 103 during the course of the scan and the factors which determine the amount of such rotation, reference should again be made to FIGS. 1 and 2. In the conventional X-ray tomographic apparatus, the successive X-ray paths 149 between the source and detector during the course of an individual scan are strictly parallel and the back projection image construction technique as hereinbefore described and as embodied in many existing computer programs for image contruction are based on the premise that this strictly rectilinear scanning action is utilized. However, by referring to FIG. 2 it may be seen that the successive X-ray paths 149' which occur during the course of a single scan in the present system are not strictly parallel but are instead convergent on the temporarily fixed position of the detector 29 giving rise to a tapered or triangular scan geometry. It is possible to obtain useful tomographic images without correcting for this difference in scan geometry since the practical result is simply some progressively increasing anamorphic compression of the tomograph image from one edge to an opposite edge. As long as the diagnostician or other observer is aware that some distortion is present, meaningful interpretations of the image can still be made. This distortion can be minimized, if desired, simply by increasing the distance between the X-ray source 28 and detector 29. However, the above-described additive rotation means for the camera 103 of the system of FIGS. 4 and 5 substantially eliminates such tomograph distortion altogether. To accomplish this result, the relative diameters of gears 133 and 150 are selected to provide a drive reduction between gear 133 and the camera 103 in which the amount of turning of gear 139 and camera 103 during the course of one half of a revolution of gear 133, and therefore during the course of a single undirectional horizontal scan motion at the X-ray source is equal to the angle $\theta$ which, as depicted in FIG. 2, is the angle between the two X-ray paths 149' at the extreme ends of the sweep. This angle $\theta$ is a function of both the distance between the X-ray source 28 and 29 and the breadth of the electron beam scan within the source at target anode plate 31 and thus may be different in different units of the system. Mathematically: Tan $\theta/2 = X/2d$ where X is the length of the electron beam scan in the X-ray source and d is the distance of the source from the detector. Referring again to FIG. 5, the diameter of gear 150 relative to that of gear 133 is selected, in any specific embodiment, to provide for additive rotation of camera 103 during the course of each X scan by an amount equal to the previously described angle $\theta$ for the particular installation. If it is contemplated that spacing between the source and the detector may be changed from time to time in a given installation or that the X direction scan breadth may be adjusted electronically, then gear 150 may be made replaceable or a selectively variable drive reduction means may be provided.

In the operation of the system of FIG. 5 to produce an X-ray tomograph, switches 123 and 142 are operated to select the particular horizontal or inclined plane between the X-ray source 74 and detector assembly 54 at which the tomograph is to be taken. Switch 119 is closed to enable transmission of X and Y beam deflection signals to the X-ray source 74 and transmission of the X beam deflection signal to oscilloscope 102 also. Switch 145 is closed to supply the relatively high frequency vertical sweep signal from oscillator 144 to the oscilloscope. Switch 131 is then temporarily set at the forward drive position for a period sufficient to enable motor 128 to effect one complete horizontal sweep of the electron beams of the X-ray source and the oscilloscope. During this period camera 103 rotates through an angle $\theta$ as previously described to correct for optical distortion and also records on film a portion of the total data needed to produce the tomograph. Switch 131 is then temporarily set at the reverse drive position to sweep the electron beams back to the original positions thereby completing a first X-scan. During this return portion of the first scan, camera 103 turns back through the angle $\theta$ to restore the original camera orientation. At the completion of the first scan, switch 131 is temporarily opened to stop the X scanning while switch 147 is momentarily closed to rotate the patient's chair 56 and camera 103 through a preferably very small angle. Switch 147 is then opened and switch 131 is again temporarily operated to complete a subsequent X scan and the recording of additional data for the tomograph image on the film in camera 103. This alternated process of X scanning operations and angular movement of the patient and camera 103 is then repeated for a large number of times preferably through 180° of rotation of the patient and the camera. Thereafter, all switches may be opened and the film is removed from camera 103 and developed to provide a transparency which constititues the desired cross-sectional tomographic X-ray image of the subject. Such a transparency may be refined as previously described, if desirable, and may be viewed directly or with the aid of a slide projector or photographic prints and photographic enlargements, may be made in the known manner.

While the above described example of the invention has an X-ray source in which a single electron beam scans along a single plane at any given time, sources having more than one electron beam simultaneously scanning along more than one spaced apart planes can also be used to generate tomographic image data for more than one plane at the same time.

In the analog data processing system as described above with reference to FIGS. 4 and 5, the camera 103 is rotated relative to the display at the face of oscilloscope 101. The necessary rotational movement is relative and thus it is equally possible to maintain the camera 103 fixed in position while the display on the face of the oscilloscope 101 is itself rotated. FIG. 8 illustrates such a modification of the oscilloscope wherein a stationary camera may be used. In the modification depicted in FIG. 8, the cathode ray tube 147 portion of the oscilloscope and the electrical controls for the tube may be of conventional construction and accordingly will not be described. Cathode ray tube 147 is suitably mounted in a housing 155 with the face of the tube being exposed at one end of the housing. Unlike the usual oscilloscope, the annular magnetic beam deflection yoke 151, including the customary X and Y magnetic poles and associated windings, is supported for rotational movement about the axis of the tube. Thus deflection yoke 151 may be secured to an annular support member 152 which is journaled by opposed thrust bearings 153 mounted in bearing retainers 154 which attach to the housing 148. A cylindrical member 156 is secured to the opposite end of the deflection yoke 151 in coaxial relationship and carries a toothed flange 157 defining a drive gear for the rotatable yoke assembly. To provide for the transmission of X and Y deflection signal voltages to the rotatable yoke 151 and to provide for a ground connection, slip rings 158 may be disposed on member 156 which is formed of insulative material. Brushes 159 are secured to an insulative stationary support 161 to ride against the slip rings.

Rotation of the magnetic deflection yoke 151 has the effect of rotating the visual display on the face of the tube 147 so that a fixed position camera may be used with the modified system. To effect the controlled rotation movements of the deflection yoke 151, the rotor shaft of a receiver synchro 112a may be journaled in a bearing 162a at the top of housing 155 and a gear 163 is mounted on the rotor shaft. Gear 163 engages the gear 157 of member 156 and is of equal diameter. Another receiver synchro 116a is mounted on top of housing 155 and has a rotor shaft which extends through another bearing 162b and is secured to the body of synchro 112a in coaxial relationship with the rotor shaft thereof. Thus the entire synchro 112a is supported for rotational movement by the other synchro 116a. Rotation of the output shaft of synchro 116a turns synchro 112a, gears 163 and 167 and thus turns the deflection yoke 151. Synchro 112a enables additive rotational motion of the deflection yoke 151 in addition to that effected by synchro 116a.

The electrical connections to the two synchros 116a and 112a may be similar to those previously described for the corresponding synchros 112 and 116 of the system of FIG. 5. The electrical connections to the rotatable synchro 112a may be made through a slip ring and brush assembly 164 mounted on housing 148 and encircling synchro 112a as depicted in FIG. 8.

The net effect of the modified structure of FIG. 8 is to effect the same rotational movements between the camera and oscilloscope display, in a relative sense, that were described with respect to the system of FIGS. 4 and 5. It should be observed that desired relative rotation between the oscilloscope display and the camera may also be realized utilizing both a fixed deflection yoke and a fixed camera by coupling appropriate electrical function generators into the X and Y sweep frequency system of the oscilloscope.

In the operation of the examples of the present invention as set forth above, the relative rotation between the patient and the scanning X-ray source — detector structure has been described as being performed intermittently with a small amount of such rotation being effected in the intervals between each X-ray scanning operation which is accomplished electronically. While this mode of operation may be preferable in many instances, it should be observed that the rotation of the patient may, if desired, be continuous and concurrent with the X-ray scanning operations. Since the above described system produces relative rotation between the recording camera and the oscilloscope display in response to both physical turning of the patient and also to the effective change of angular relationship resulting from the tapered or triangular geometry of the X-axis scanning, the data processing system 99 automatically adjusts to both actual rotation of the patient and to effective rotation because of the tapered geometry of the scan, whenever either effect occurs. Thus, if desired, the patients' chair drive motor 128 of FIG. 5 may be operated continuously to bring about 180° of rotation of the patient, for example, during the time the X-ray source repeatedly scans back and forth. Camera 103 simply turns as necessary in response to both actions in such a manner as to record on film the desired tomographic image data.

The time required to prepare a tomographic image and the amount of angular rotation of the patient relative to the other structure that is needed to produce an image of given resolution and clarity may be reduced by employing more than one scanning X-ray source and detector and more than one oscilloscope and camera as depicted in FIG. 9. In such a system the subject 52b may again be situated between a scanning X-ray source 53b and detector 87b in the manner previously described. Collimators for the source 53b and detector 87b and preamplifiers, amplifiers and pulse discriminators for the X-ray detector output signals may be similar to those previously described and are accordingly not depicted in FIG. 9. The patient 52b is again rotatable relative to the X-ray source and detector by a motor 67b coupled to a power supply 29c through a control switch 147c. A variable X-deflection voltage and a selectable level Y-deflection voltage are applied to scanning source 53b by a deflection signal generator 166 to establish the X scanning action and to establish the vertical level of the plane to be scanned. The internal construction of the deflection signal generator 166 may be similar to the corresponding portion of the previously described system of FIG. 4 and accordingly will not be redescribed. Also, as in the previously described system, the deflection signal generator circuit drives the rotor of a transmittor synchro 148b, which is electrically coupled to a receiver synchro 112b. The rotor of synchro 112b turns a camera 103b which views the screen or face of an oscilloscope 101b. Receiver synchro 112b is rotatable as a unit as it is coupled to the rotor of another fixed receiver synchro 116b. Synchro 116b is in turn electrically coupled to a transmittor synchro 69b having a rotor mechanically coupled to undergo synchronous rotation with the patient 52b. Accordingly, camera 103b rotates relative to the display at the face of oscilloscope 101b in correspondence with rotation of the patient 52b relative to the X-ray source and detector. Superimposed upon such camera rotation is an additive turning motion in the course of each X-ray scan of the patient 52b. The X or horizontal sweep terminal of the oscilloscope 101b receives the same variable X deflection signal as does the scanning X-ray source 53b while a relatively high frequency alternating vertical sweep signal is applied to the Y terminal of the oscilloscope from an oscillator 144b. The Z or intensity terminal of the oscilloscope 101b receives the amplified and shaped output X-ray signals from the detector 87b.

The above-described components which control scanning X-ray source 53b and oscilloscope 101b and which respond to the output of detector 87b may be identical to the corresponding components of the previously described embodiment of FIGS. 4 and 5 and therefore are depicted somewhat more diagramatically in FIG. 9. The system differs from the previously described embodiment in that additional scanning X-ray sources 53c and 53d, additional detectors 87c and 87d, additional oscilloscopes 101c and 101d, and additional cameras 103c and 103d are employed.

Source 53c and the associated detector 87c are disposed on opposite sides of the patient 52b along a center line forming an angle of 120° with the center line of source 53b and detector 87b. Similarly, the third source 53d and the third X-ray detector 87d are disposed on opposite sides of the patient 52b along a line inclined 120° to the axis of both of the other sources 53b and 53c. Each of the additional sources 53c and 53d may be coupled to the deflection signal generator 166 to receive the same X and Y deflection signals. Thus all three sources 53 scan the subject 52b synchronously from different angles. If it is desired to reduce the irradiation rate or if other considerations make it desirable each of the sources 53 may be provided with independent controls so that scanning of the patient by each source may be accomplished in sequence rather than simultaneously.

Each of the additional oscilloscopes 101c and 101d has an X-sweep terminal connected in parallel with that of oscilloscope 101b and has a Y or vertical sweep terminal connected in parallel with the Y terminal of oscilloscope 101b, so that all three oscilloscopes simultaneously undergo similar horizontal and vertical sweep movements. However, the Z or intensity control of oscilloscope of 101c receives the output of X-ray detector 87c in particular while the Z terminal of oscilloscope 101d receives the output of X-ray detector 87d, in particular.

All three cameras 103 are mechanically coupled together for synchronous rotation with the rotor of synchro 112b but each camera is inclined at a 120° angle relative to the other cameras. Thus, camera 103c is always turned 120° in this example, relative to camera 103b, while camera 103d is turned another 120° relative to camera 103c.

The system of FIG. 9 is operated in a manner essentially similar to the operation of the previously described embodiment in that the patient 52b is turned angularly relative to the X-ray sources and detectors by motor 67b while repetitive X-ray scans of a selected plane through the patient 52b are performed by each of the X-ray sources 53. Because three angularly spaced source and detector units are present, a tomographic image of a given degree of resolution and clarity, requires one-third of the number of X scans from any particular source 53 and one-third of the angular movement of the patient 52b, relative to the sources that would be required by a single source and detector unit.

The film which is removed from any particular one of the cameras 103b will, upon development, contain only one-third of the total image data. The three film transparencies may then be overlaid as previously described and depicted with reference to FIG. 3B to produce the desired image. If a broad light source is viewed through the overlaid transparency, the desired image is visible. The image may be refined as previously described with reference to FIG. 3C.

The system as depicted in FIG. 9 utilizes three scanning X-ray sources 53, three detectors 87 and three oscilloscopes 101 for purposes of example only. A larger number of each may be employed with smaller angular spacing if it is desired to further decrease the time of the scanning procedure and to further reduce the amount of angular movement which must be provided for. It is in fact possible, by utilizing a very large number of X-ray sources and detectors in the general arrangement depicted in FIG. 9, to obtain the desired tomographic image without any angular motion of a patient 52b relative to the sources whatsoever although in many cases the resulting increase in the size, complexity and cost of the system may not be warranted for economic reasons.

The embodiments of the invention described above scan through the subject along a planar area which is of a tapered or triangular configuration. As previously discussed, this scan configuration causes some distortion in the image unless the previously described data processing means for supressing the distortion is used. It is possible to construct a modified form of the present invention which performs a strictly rectilinear scan having a geometry similar to that of conventional tomographic X-ray systems. The modified forms of the invention may employ the existing digital computer programs for constructing tomographic images without requiring additional means or program modifications to produce an undistorted image. A modification of the invention of this kind is illustrated in FIG. 10.

In the system of FIG. 10, the scanning X-ray source 53e, the X-ray detector assembly 54e and the subject 52e which is to be scanned and which is situated between the source and detector are depicted in plan view. In other words, the plane along which the subject 52e is scanned lies in the plane of the drawing or parallel thereto except when the apparatus is operated to scan oblique planes, as will be hereinafter discussed. For convenience of description, FIG. 10 will be regarded as a top view of the source 53e, subject 52e and detector 54e, although it should be understood that there is no absolute requirement that the subject be rotated about a vertical axis and scanned in a horizontal plane.

The scanning source 53e may be similar to those previously described wherein an electron beam 78e is systematically scanned back and forth in a horizontal plane, to produce a moving origin point of X-rays, by an X-axis deflection signal, the vertical level of the predetermined path of the electron beam on the target end of plate 79e being determined by a Y-deflection signal voltage. A conventional sawtooth wave generator 167 may be used to generate the X-deflection signal and for this purpose may have an output connected to the X-axis deflection signal terminals of source 53e through a switch 168 and an isolation amplifier 127e. When utilizing a sawtooth wave generator, the moving point source of X-ray always progresses from one side of the target end plate 79e to the other in the course of each scan. Sawtooth wave generator 167 may, if desired, be replaced with a triangular wave generator, in which case the point of X-ray origin sweeps back and forth across the target anode plate in the course of each scan.

To provide a selectable Y-axis deflection signal to the X-ray source for determining the height of the plane at which the subject is scanned a selectable voltage may be produced by a potentiometer 169 having a resistive element connected across a D.C. voltage source 118e through a control switch 119e and having a variable voltage tap connected to the Y-axis deflection terminal of source 53e through an isolation amplifier 122e.

The subject 52e to be scanned is disposed for controlled angular motion about a vertical axis in this example and may be selectively turned by a electrical motor 67e coupled to suitable power supply 129e through a control switch 147e. As in the previously described embodiments, a transmitter synchro 69e produces a signal indicative of the angular position of subject 52e which signal operates a receiver synchro 112e that turns a camera 103e in synchronism with rotary movement of the subject. The camera 103e is positioned to view the face of an oscilloscope 101e in order to record a tomographic image by the electro-optical process previously described with respect to other embodiments of the invention. It should be observed that the receiver synchro 112e which turns the camera 103e in this embodiment may be electrically coupled directly to the transmitter synchro 69e without the intervening supplementary synchro structure employed in the previous embodiments since the X-ray scan is rectilinear in this case and there is no optical distortion, arising from tapered geometry, to be corrected for. As in the previous embodiments, the X or horizontal sweep signal terminal of oscilloscope 101e receives the same deflection signal that is delivered to the source 53e. Also, an oscillator 144e having an output frequency substantially higher than the frequency of sawtooth wave generator 167 is coupled to the Y or vertical sweep frequency terminal of oscilloscope 101e through a switch 145e for purposes similar to those previously described.

The X-ray detector assembly 54e in this embodiment differs considerably from that of the previously described examples in that the scintillator 88e which generates visible light in response to X-rays is a long rod-like element disposed horizontally in this example in order to lie in the plane of the X-ray scan of the subject and in parallel relationship to source target anode plate 79e. Preferably scintillator 88e has a length at least equal to the scan path of the electron beam of the source 53e to provide for the desired rectilinear scan geometry. A tapered light pipe 91e extends between scintillator 88e and a photomultiplier tube 89e to transmit scintillations of light from any portion of the long scintillator to the phototube in order to generate electrical X-ray count signals. The count signals are then transmitted through a preamplifier 137e and a shaper amplifier 138e and then to the Z-axis or intensity control terminal of oscilloscope 101e.

Referring now to FIG. 11 in conjunction with FIG. 10, a thick radiation absorbent collimator 83e is disposed adjacent the target end of the X-ray source and another collimator 94e extends along the face of the X-ray detector assembly 54e adjacent a plate 55e which is radiation transmissive but opaque to visible light to prevent external light from reaching the scintillator 88e. Source collimator 83e has a large number of narrow radiation transmissive passages 86e which are aligned in parallel relationship when seen in horizontal cross section as shown in FIG. 10, but which preferably converge towards the detector scintillator 88e when seen in vertical cross section as depicted in FIG. 11. The detector collimator 94e also has a row of narrow radiation transmissive passages 86e which are parallel when seen in horizontal section as depicted in FIG. 10 and which, as shown in FIG. 11, are convergent towards the scintillator 88e when seen in elevation section with the vertical extent of such passages 86e being at least sufficient to subtend all those of the passages 86e of the source collimator 83e along which X-ray scans may be made. Alternatively, the detector collimator 94e may have a number of vertically spaced rows of circular passages convergent on the scintillator 88e in a manner essentially similar to the construction of the source collimator 83e.

In connection with the previously described embodiments, it has been pointed out that while a collimator may be advantageously used at the X-ray source and another collimator may be used at the X-ray detector assembly, neither collimator is absolutely essential from the standpoint of producing a tomographic image. The basic purpose of the collimators in the previously described embodiment are to improve image clarity and to reduce radiation dosage of the subject. In the system of FIGS. 10 and 11, at least one collimator must of necessity be situated between the X-ray source and the X-ray detector assembly in order to obtain an image and preferably both collimators are used. In the absence of any collimation in the system of FIG. 10, scintillations will tend to occur simultaneously along the length of scintillator 88e from X-rays arriving from various directions. Without the collimator, the system of FIG. 10 could not distinguish X-ray counts which are significant to construction of the desired image from those which are not.

Aside from the rectilinear scanning geometry and differences arising from the above-described modified construction of the X-ray detector assembly 54e, the operation of the system of FIGS. 10 and 11 is essentially similar to that of the previously described embodiments. The vertical level of the plane through the subject 52e which is to be imaged is determined by setting potentiometer 169 and to facilitate this operation, a voltmeter 171 may be connected between the movable tap of the potentiometer and ground so that any of a plurality of predetermined vertical deflection voltages may be applied to the X-ray source. By closing switch 168, one or more horizontal X-ray scans of the subject 52e may be made and then the subject 52e may be rotated relative to the X-ray source and detector assembly by temporarily closing drive motor control switch 147e. This sequence of X-ray scanning and angular repositioning is then repeated many times preferably until the angular position of the subject 52e relative to the X-ray source and detector assembly has progressed through 180° of arc. The shutter of camera 103e is opened during the scanning procedure and the camera and oscilloscope 101e coact to produce a film which may be developed to produce the desired tomographic X-ray image in the manner hereinbefore described.

The system of FIG. 10 may produce an image for a single horizontal plane transacting the subject 52e or for any of a number of inclined planes, depending on the Y deflection signal voltage applied to the X-ray source from potentiometer 169. If it is desired to produce images at any of a plurality of vertically spaced horizontal planes without vertical movement of the subject 52e or the X-ray source and detector assemblies, additional detector assemblies consisting of additional scintillators 88e, light pipes 91e and phototubes 89e may be situated in the detector assembly 54e above or below the one depicted in FIG. 10.

The system described with reference to FIGS. 10 and 11 utilizes a long continuous scintillator 88e in the X-ray detector assembly 54e. As shown in FIG. 12, an otherwise similar system may be constructed in which the X-ray detector assembly 54f has a plurality of minute scintillators 88f or other small X-ray detectors disposed in the plane of the X-ray scan and spaced apart in the direction of scanning. Each scintillator 88f may be mounted on the end of an associated individual light pipe 91f which transmits X-ray originated scintillations of light to an associated individual one of a plurality of photomultiplier tubes 89f. The count signal output conductors 173 of each of the photomultiplier tubes connect with the Z terminal of the oscilloscope 101f through an associated individual preamplifier 137f and shaper amplifier 138f. While a detector collimator 94f may be situated in front of the scintillators 88f to improve image clarity and may be similar to the corresponding collimator of the system of FIGS. 10 and 11, the modified detector of FIG. 12 is capable of producing an image which no collimation structure between the X-ray source in the X-ray detectors. An image with no collimation structure may also be obtained using a single detector of the position sensitive type.

The several embodiments of the invention described above, generate signals which, taken in conjunction, contain the information needed to construct a tomographic, cross-sectional X-ray image of a subject. The examples of the invention which have been heretofore described have employed a novel analog system to perform the actual image production on photographic film. The invention is also compatible with use of digital data processing techniques using known systems, if desired, to generate the visible image or to otherwise record the data. FIG. 13 depicts how the previously described systems may be coupled to a minicomputer 174 which in turn controls an oscilloscope 176 to produce the desired sectional tomographic X-ray image at the screen 176 of the oscilloscope. Minicomputer 174 may, for example, be the well known model identified as the Eclipse, manufactured by Data General Corporation. Suitable programs 177 enabling the computer to operate an oscilloscope 176 to produce a computed tomographic X-ray image are known to the art, one example being identified as the LSC algorithm and being described by Cho in the June 1974 issue of IEEE Transactions on Nuclear Sciene, flow chart diagrams for that computer program being given on pages 70 and 71 of the publication.

In order to provide the necessary input information for computer 174, certain of the signals generated by the present invention must be digitized where such signals are not already in digital form. Considering a first such input, a digital signal indicative of the instantaneous angular position of the subject relative to the X-ray source and detector structure must be provided. For this purpose, a known digitizer 178 of the form which generates a digital signal indicative of the position of a rotatable shaft may be coupled to the computer 174 through a standard interface card 179a. The rotary input of the digitizer 178 may be mechanically coupled to the rotor shaft of the previously described synchro 112.

The computer is also supplied with a digital input signal indicative of the vertical level of the X-ray scan plane. For this purpose, the previously described movable contact 123 of the Y deflection signal voltage selector switch may be coupled to the computer through an analog to digital converter 181 and standard interface card 182. Analog to digital converter 181 may be of the well known form having an output at which a binary coded signal appears indicative of the magnitude of a D.C. voltage applied to the input.

Similarly, the computer must be supplied with data indicative of the progress of the X scanning motion of the X-ray source, and for this purpose the rotating wiper 126 of the previously described X deflection signal generating circuit may be coupled to another analog to digital converter 183 having an output coupled to the computer through another interface card 184.

Unlike the previously described inputs to the computer 174, the count signal pulses produced by the present invention are already in an essentially digital form and may be transmitted directly to the computer through still another standard interface card 186. For this purpose, the input of the interface card may be connected to the previously described channel selector switch 142.

The above-identified computer, when programmed with the above-identified program, processes the input information to generate X sweep, Y sweep and Z or intensity signals for controlling an oscilloscope 176 to cause the desired tomographic image to be displayed. For this purpose, the X, Y and Z signal outputs of the computer may be coupled to the corresponding terminals of the oscilloscope through additional interface cards 187 and digital to analog converters 188 of the known form which produce a D.C. output voltage having a magnitude determined by a digital input signal. The computer may, if desired, also be programmed to control the cycling of the previously described switches.

While the invention has been described with respect to certain representative embodiments, it will be apparent that many modifications are possible and it is not intended to limit the invention except as defined in the following claims.

What is claimed is:

1. Tomographic X-ray apparatus comprising:
   at least one scanning X-ray source having an anode plate and an electron gun for directing at least one electron beam toward said anode plate and having first beam deflection means for sweeping said electron beam relative to said anode plate to produce X-rays at successive points along a predetermined path on said anode plate, said X-ray source also having means for producing a first deflection signal which varies in accordance with the position of the moving point of impact of said electron beam on said anode plate along said predetermined path,
   at least one X-ray detector spaced from said source whereby a subject to be scanned may be disposed therebetween, said detector having at least one active X-ray-sensitive area substantially smaller than the area of said anode plate of said source with all active radiation-sensitive area being confined to a region no broader than the length of said predetermined path and having means for producing count signals indicative of X-rays received along a plurality of successive X-ray paths extending from said successive points on said anode plate to said detector,
   a rotational positioning device for effecting predetermined relative angular motion between said subject and said source and detector structure and having means for producing a first angular position signal indicative of the angular relationship of said subject to said source and detector structure, and
   a data processing system coupled to said X-ray source and said detector and said rotational positioning device to receive said signals therefrom and having means for determining variations of X-ray transmissiveness at different areas of said subject from said signals which different areas of said subject lie on the surface defined by said plurality of successive X-ray paths.

2. Apparatus as defined in claim 1 wherein said data processing system includes means for storing data indicative of said X-ray transmissiveness of different areas of said subject.

3. Apparatus as defined in claim 1 wherein said data processing system includes means for displaying a visual image of said variations of X-ray transmissiveness of said different areas of said subject.

4. The apparatus defined in claim 1 further comprising means for producing a second angular position signal indicative of movement of said moving point of impact of said electron beam along said predetermined path, and means for transmitting said second angular position signal to said data processing system.

5. The apparatus defined in claim 1 wherein said X-ray detector has a linear X-ray sensitive element extending parallel to said predetermined path of said X-ray source and further comprising at least one X-ray absorbant collimator disposed between said source and said detector and having a plurality of X-ray transmissive passages oriented to transmit X-rays originating at successive points along said predetermined path at said source to predetermined successive points along said X-ray sensitive element.

6. The apparatus defined in claim 5 wherein said passages of said collimator are parallel and spaced apart.

7. The apparatus defined in claim 1 wherein said X-ray detector has a plurality of X-ray sensitive elements spaced apart in a direction parallel to that of said predetermined path of said X-ray source.

8. The apparatus defined in claim 1 wherein said data processing system comprises a digital computer.

9. The apparatus defined in claim 6 wherein said digital computer is programmed to generate vertical and horizontal sweep signals and intensity signals for controlling an oscilloscope display to produce a computed tomographic sectional X-ray image transacting said subject, further comprising an oscilloscope coupled to said computer for receiving said signals therefrom.

10. Tomographic X-ray apparatus comprising:
- at least one scanning X-ray source having an anode plate and an electron gun for directing at least one electron beam toward said anode plate and having first beam deflection means for sweeping said electron beam relative to said anode plate to produce X-rays at successive points along a predetermined path on said anode plate, said X-ray source also having means for producing a first deflection signal which varies in accordance with the position of the moving point of impact of said electron beam on said anode plate along said predetermined path,
- at least one X-ray detector spaced from said source whereby a subject to be scanned may be disposed therebetween, said detector having at least one active X-ray-sensitive area substantially smaller than the area of said anode plate of said source and having means for producing count signals indicative of X-rays impinging on said sensitive area,
- a rotational positioning device for effecting predetermined relative angular motion between said subject and said source and detector structure and having means for producing a first angular position signal indicative of the angular relationship of said subject to said source and detector structure,
- a data processing system coupled to said X-ray source and said detector and said rotational positioning device to receive said signals therefrom and having means for determining variations of X-ray transmissiveness at different areas of said subject from said signals,
- wherein said data processing system comprises an oscilloscope having means for producing a light area at a face thereof in response to signals received at a Z-axis terminal and having means for shifting the position of said light area in a first direction in response to a first sweep signal received at an X-axis terminal and having means for shifting the position of said light area in a second orthogonal direction in response to a second sweep signal received at a Y-axis terminal,
- means for transmitting count signals from said X-ray detector to said Z-axis terminal,
- means for transmitting said first deflection signal to said X-axis terminal,
- an oscillator having an output coupled to said Y-axis terminal, said oscillator having an output frequency substantially greater than the sweep frequency of said first deflection means to convert said light area on said face of said oscilloscope to a display of bands of light extending in said second direction,
- a camera positioned to view said face of said oscilloscope to photographically record said display of bands of light, and
- first means for producing relative rotation between said camera and said display at said face of said oscilloscope corresponding to said predetermined relative angular motion between said subject and said source and detector structure.

11. The apparatus defined in claim 10 wherein said first means for producing relative rotation comprises means supporting said camera for rotation relative to said face of said oscilloscope, and means coupling said camera to said rotational positioning device for synchronous rotation therewith.

12. The apparatus defined in claim 10 wherein said oscilloscope has a beam deflector of the form which shifts said light area in said first direction and in said second direction in response to signals received at said X-axis terminal and said Y-axis terminal respectively, further comprising:
- means supporting said beam deflector for angular movement relative to other components of said oscilloscope, and means coupling said deflector yoke to said rotational positioning device for synchronous rotation therewith.

13. The apparatus defined in claim 10 further comprising second means for producing relative rotation between said camera and said display at said face of said oscilloscope as said point of impact of said electron beam on said anode plate of said X-ray source moves along said predetermined path.

14. Tomographic X-ray apparatus comprising:
- at least one scanning X-ray source having an anode plate and an electron gun for directing at least one electron beam toward said anode plate and having first beam deflection means for sweeping said electron beam relative to said anode plate to produce X-rays at successive points along a predetermined path on said anode plate, said X-ray source also having means for producing a first deflection signal which varies in accordance with the position of the moving point of impact of said electron beam on said anode plate along said predetermined path,
- a plurality of X-ray detectors spaced from said source whereby a subject to be scanned may be disposed therebetween, each of said detectors having at least one active X-ray-sensitive area substantially smaller than the area of said anode plate of said source and having means for producing count signals indicative of X-rays impinging on said sensitive area, said sensitive areas of said detectors being spaced apart along a line which extends orthogonally with respect to said predetermined path on said anode plate of said X-ray source,
- a rotational positioning device for effecting predetermined relative angular motion between said subject and said source and detector structure and having means for producing a first angular position signal indicative of the angular relationship of said subject to said source and detector structure,
- a data processing system coupled to said X-ray source and said detector and said rotational positioning device to receive said signals therefrom and having means for determining variations of X-ray transmissiveness at different areas of said subject from said signals, and
- second beam deflection means at said X-ray source for selectively shifting said predetermined path of electron impact on said anode plate in a direction orthogonal to said predetermined path.

15. The apparatus defined in claim 14 further comprising at least an additional one of said X-ray sources positioned to direct X-rays towards said subject from a different angle within the planes defined by said predetermined path and said plurality of X-rays detectors, and at least an additional plurality of said X-ray detectors disposed on the opposite side of said subject from said additional one of said X-ray sources.

16. The apparatus defined in claim 14 wherein each of said X-ray detectors has a linear X-ray-sensitive element extending parallel to said predetermined path of said X-ray source and further comprising at least one X-ray absorbent collimator disposed between said source and each of said detectors and having a plurality of X-ray-transmissive passages oriented to transmit X-rays originating at successive points along said predetermined path at said source to predetermined successive points along said X-ray-sensitive element.

17. In a method for producing X-ray tomographic image data for a plane transecting a subject, the steps comprising:
- disposing said subject between an X-ray detector having at least one radiation-sensitive area and a scanning X-ray source wherein an electron beam may be swept across a broad target to produce a moving X-ray origin point,
- operating said X-ray source to scan said subject by generating X-rays at a moving origin point which travels along a predetermined path lying in said plane,
- generating X-ray count signals from said X-ray detector during said scan which are indicative of X-rays received along a plurality of successive X-ray paths extending from said moving origin point to said detector and lying in said plane which transects said subject, including intercepting at a radiation-sensitive area of said detector substantially all X-rays from said origin point which pass through said subject at said plane and concurrently generating scan position signals indicative of the location of said moving origin point along said predetermined path at which said count signals are produced,
- changing the angular relationship of said subject relative to said source and detector at least once, and
- repeating said scan of said subject at least once while again generating X-ray count signals and scan position signals.

18. In a method as defined in claim 17, the further step comprising generating first rotational position signals as the angular relationship of said subject relative to said source and detector is changed.

19. In a method as defined in claim 17, the further step comprising transmitting said signals to a digital computer programmed to construct a visible tomographic image from said signals.

20. In a method for producing X-ray tomographic image data for a plane transecting a subject, the steps comprising:
- disposing said subject between an X-ray detector and a scanning X-ray source wherein an electron beam may be swept across a broad target to produce a moving point X-ray origin point,
- operating said X-ray source to scan said subject by generating X-rays at a moving origin point which travels along a predetermined path lying in said plane,
- generating X-ray count signals from said X-ray detector during said scan and concurrently generating scan position signals indicative of the location of said moving origin point along said predetermined path at which said count signals are produced,
- changing the angular relationship of said subject relative to said source and detector at least once,
- repeating said scan of said subject at least once while again generating X-ray count signals and scan position signals,
- utilizing said X-ray count signals to control the intensity of the light display at the face of an oscilloscope,
- sweeping said light display at said oscilloscope in a first direction on said face in synchronism with motion of said moving X-ray origin point along said predetermined path of said X-ray source,
- repetitively sweeping said light display in a second direction which is orthogonal to said first direction at a rate exceeding the rate of movement of said light display in said first direction,
- utilizing a camera containing a film to photograph said face of said oscilloscope during each of said scans of said subject,
- producing relative rotation between said camera and said display in synchronism with said changes of the angular relationship between said subject and said source and detector, and
- developing said film to produce a tomographic sectional image of said subject.

21. In a method as defined in claim 20, the further step comprising producing relative rotation of said camera and said display during each of said scans, said relative rotation being through an angle equal to the angle which said predetermined path subtends at said X-ray detector.

22. Tomographic X-ray apparatus for examining planes within a subject comprising:
- at least one scanning X-ray source having an anode plate and an electron gun for directing at least one electron beam toward said anode plate and having first beam deflection means for sweeping said electron beam relative to said anode plate to produce X-rays at successive points along a predetermined electronic scanning path on said anode plate, said electronic scanning path lying in a plane to be examined, said X-ray source also having means for producing a first deflection signal which varies in accordance with the position of the moving point of impact of said electron beam on said anode plate along said predetermined electronic scanning path,
- a plurality of X-ray detectors spaced from said source whereby a subject to be scanned may be disposed therebetween, each of said detectors having at least one active X-ray-sensitive area substantially smaller than the area of said anode plate of said source and having means for producing count signals indicative of X-rays impinging on said sensitive area, said sensitive areas of said detectors being spaced apart along a line which extends orthogonally with respect to said predetermined electronic scanning path on said anode plate of said X-ray source,
- a rotational positioning device for effecting predetermined relative angular motion between said subject and said source and detector structure and having means for producing a first angular position signal indicative of the angular relationship of said subject to said source and detector structure, and
- a data processing system coupled to said X-ray source and said detector and said rotational positioning device to receive said signals therefrom and having means for determining variations of X-ray transmissiveness at different areas of said subject from said signals.

23. Tomographic X-ray apparatus comprising:
- at least one scanning X-ray source having an anode plate and an electron gun for directing at least one electron beam toward said anode plate and having first beam deflection means for sweeping said electron beam relative to said anode plate to produce X-rays at successive points along a predetermined path on said anode plate, said X-ray source also having means for producing a first deflection signal which varies in accordance with the position of the moving point of impact of said electron beam on said anode plate along said predetermined path, a plurality of X-ray detectors spaced from said source whereby a subject to be scanned may be disposed therebetween, each of said detectors having at least one active X-ray-sensitive area substantially smaller than the area of said anode plate of said source and having means for producing count signals indicative of X-rays impinging on said sensitive area, said sensitive areas of said detectors being spaced apart along a line which extends orthogonally with respect to said predetermined path on said anode plate of said X-ray source, a rotational positioning device for effecting predetermined relative angular motion between said subject and said source and detector structure and having means for producing a first angular position signal indicative of the angular relationship of said subject to said source and detector structure, a data processing system coupled to said X-ray source and said detector and said rotational positioning device to receive said signals therefrom and having means for determining variations of X-ray transmissiveness at different areas of said subject from said signals, and a multiple position switch coupled between said plurality of said detectors and said data processing system and having means for transmitting said count signals from any selected one of said detectors to said data processing system.

24. Tomographic X-ray apparatus comprising:

at least one scanning X-ray source having an anode plate and an electron gun for directing at least one electron beam toward said anode plate and having first beam deflection means for sweeping said electron beam relative to said anode plate to produce X-rays at successive points along a predetermined path on said anode plate, said X-ray source also having means for producing a first deflection signal which varies in accordance with the position of the moving point of impact of said electron beam on said anode plate along said predetermined path, at least one X-ray detector spaced from said source whereby a subject to be scanned may be disposed therebetween, said detector having at least one active X-ray-sensitive area substantially smaller than the area of said anode plate of said source and having means for producing count signals indicative of X-rays impinging on said sensitive area, a rotational positioning device for effecting predetermined relative angular motion between said subject and said source and detector structure and having means for producing a first angular position signal indicative of the angular relationship of said subject to said source and detector structure, a data processing system coupled to said X-ray source and said detector and said rotational positioning device to receive said signals therefrom and having means for determining variations of X-ray transmissiveness at different areas of said subject from said signals, means for producing a second angular position signal indicative of movement of said moving point of impact of said electron beam along said predetermined path, and means for transmitting said second angular position signal to said data processing system, and means utilizing said second angular position signal for compensating for the tomographic distortion which would otherwise result from the non-parallelism of the rays from the moving point of impact to said X-ray detector.

25. Tomographic X-ray apparatus comprising:

at least one scanning X-ray source having an anode plate and an electron gun for directing at least one electron beam toward said anode plate and having first beam deflection means for sweeping said electron beam relative to said anode plate to produce X-rays at successive points along a predetermined path on said anode plate, said scanning X-ray source also having means for producing a first deflection signal which varies in accordance with the position of the moving point of impact of said electron beam on said anode plate along said predetermined path, at least one X-ray detector spaced from said scanning X-ray source whereby a subject to be scanned may be disposed therebetween, said detector having at least one active X-ray-sensitive area substantially smaller than the area of said anode plate of said scanning X-ray source and having means for producing count signals indicative of X-rays impinging on said sensitive area, a rotational positioning device for effecting predetermined relative angular motion between said subject and said scanning X-ray source and detector structure and having means for producing a first angular position signal indicative of the angular relationship of said subject to said scanning X-ray source and detector structure, a data processing system coupled to said scanning X-ray source and said detector and said rotational positioning device to receive said signals therefrom and having means for determining variations of X-ray transmissiveness at different areas of said subject from said signals, at least an additional one of said scanning X-ray sources positioned to direct X-rays towards said subject from a different angle within the plane defined by said predetermined path and said X-ray detector, and at least an additional one of said X-ray detectors disposed on the opposite side of said subject from said additional scanning X-ray source.

26. In a method for producing X-ray tomographic image data for a plane transecting a subject, the steps comprising:

disposing said subject between an X-ray detector having at least one radiation-sensitive area and a scanning X-ray source wherein an electron beam may be swept across a broad target to produce a moving X-ray origin point, operating said X-ray source to scan said subject by generating X-rays at a moving origin point which travels along a predetermined path lying in said plane, generating X-ray count signals from said X-ray detector during said scan which are indicative of X-rays received along a plurality of successive X-ray paths extending from said moving origin point to said detector and lying in said plane which transects said subject, including intercepting at a radiation-sensitive area of said detector substantially all X-rays from said origin point which pass through said subject at said plane and concurrently generating scan position signals indicative of the location of said moving origin point along said predetermined path at which said count signals are produced, changing the angular relationship of said subject relative to said source and detector at least once, repeating said scan of said subject at least once while again generating X-ray count signals and scan position signals, generating first rotational position signals as the angular relationship of said subject relative to said source and detector is changed, and utilizing said X-ray count signals and said scan position signals and said rotational position signals to construct a visible tomograph image of said subject.

27. In a method for producing X-ray tomographic image data for a plane transecting a subject, the steps comprising:

disposing said subject between an X-ray detector and a scanning X-ray source wherein an electron beam may be swept across a broad target to produce a moving point X-ray origin point, operating said X-ray source to scan said subject by gneerating X-rays at a moving origin point which travels along a predetermined path lying in said plane, generating X-ray count signals from said X-ray detector during said scan and concurrently generating scan position signals indicative of the location of said moving origin point along said predetermined path at which said count signals are produced, changing the angular relationship of said subject relative to said source and detector at least once, repeating said scan of said subject at least once while again generating X-ray count signals and scan position signals, generating first rotational position signals as the angular relationship of said subject relative to said source and detector is changed, and generating a second rotational position signal during the course of each of said scans and utilizing said second rotational position signal for compensating for the tomographic distortion which would otherwise be caused by non-parallelism of the rays from the moving origin point to said X-ray detector.

28. In a method for producing X-ray tomographic image data for a plane transecting a subject, the steps comprising:

disposing said subject between an X-ray detector having at least one small radiation-sensitive area and a scanning X-ray source wherein an electron beam may be swept across a broad target to produce a moving X-ray origin point, said one radiation-sensitive area being of less extent than said subject in a direction parallel to the path of said moving X-ray origin point, operating said X-ray source to scan said subject by generating X-rays at a moving origin point which travels along a predetermined path lying in said plane and which is of sufficient length to cause X-rays to pass from said path to said radiation-sensitive area through all portions of said subject which are intersected by said plane, intercepting at said radiation-sensitive area substantially all X-rays from said moving origin point which pass through said subject along said plane, generating X-ray count signals from said X-ray detector during said scan which are indicative of X-rays received along a plurality of successive X-ray paths extending from said moving origin point to said detector and lying in said plane which transects said subject, and concurrently generating scan position signals indicative of the location of said moving origin point along said predetermined path at which said count signals are produced, changing the angular relationship of said subject relative to said source and detector at least once, and repeating said scan of said subject at least once while again generating X-ray count signals and scan position signals.

29. Tomographic X-ray apparatus comprising:

at least one scanning X-ray source having an electron-impervious but X-ray-transmissive anode plate and an electron gun for directing at least one electron beam to impact against an inner surface of said anode plate to produce X-rays which are emitted from an opposite outer surface of said anode plate and having first beam deflection means for sweeping said electron beam relative to said anode plate to produce said X-rays at successive points along a predetermined path on said anode plate, said X-ray source also having means for producing a first deflection signal which varies in accordance with the position of the moving point of impact of said electron beam on said anode plate along said predetermined path, at least one X-ray detector spaced from said X-ray source to receive said X-rays which are emitted from said outer surface of said anode plate whereby a subject to be scanned may be disposed between said X-ray source and said detector, said X-ray detector having at least one active X-ray-sensitive area substantially smaller than the area of said anode plate of said source and having means for producing count signals indicative of X-rays impinging on said sensitive area, and a data processing system coupled to said X-ray source and said X-ray detector to receive said signals therefrom to enable determination of variations of X-ray-transmissiveness at different areas of said subject from said signals which different areas of said subject lie on the surface defined by said plurality of successive X-ray paths.

30. Tomographic X-ray apparatus comprising:

at least one scanning X-ray source having an anode plate and an electron gun for directing at least one electron beam toward said anode plate and having first beam deflection means for sweeping said electron beam relative to said anode plate to produce X-rays at successive points along a predetermined path on said anode plate, said scanning X-ray source also having means for producing a deflection signal which varies in accordance with the position of the moving point of impact of said electron beam on said anode plate along said predetermined path, at least one X-ray detector spaced from said scanning X-ray source whereby a subject to be scanned may be disposed therebetween, said detector having at least one active X-ray-sensitive area substantially smaller than the area of said anode plate of said scanning X-ray source and having means for producing count signals indicative of X-rays impinging on said sensitive area, a rotational positioning device for effecting predetermined relative angular motion between said subject and said scanning X-ray source and detector structure and having means for producing a first angular position signal indicative of the angular relationship of said subject to said scanning X-ray source and detector structure, a data processing system coupled to said scanning X-ray source and said detector and said rotational positioning device to receive said signals therefrom and having means for determining variations of X-ray transmissiveness at different areas of said subject from said signals, wherein said data processing system comprises a visual display device having means for controlling light emission at a movable linear region on a face thereof in response to signals received at a Z-axis intensity signal terminal and having means for laterally shifting the position of said movable linear region on said face in response to a deflection signal received at an X-axis sweep signal terminal, means for transmitting count signals from said X-ray detector to said Z-axis terminal, means for transmitting said deflection signal to said X-axis sweep signal terminal, image recording means positioned to view said face of said visual display device to record the display of light thereon, and first means for producing relative rotation between said image recording means and said display of light at said face of said visual display device corresponding to said predetermined relative angular motion between said subject and said source and detector structure.

31. Tomographic X-ray apparatus comprising:

a first scanning X-ray source having an anode plate and an electron gun for directing at least one electron beam toward said anode plate and having first beam deflection means for sweeping said electron beam relative to said anode plate to produce X-rays at successive points along a predetermined path on said anode plate, said first scanning X-ray source also having means for producing a first deflection signal which varies in accordance with the position of the moving point of impact of said electron beam on said anode plate along said predetermined path, a first X-ray detector spaced from said first scanning X-ray source whereby a subject to be scanned may be disposed therebetween, said first X-ray detector having at least one active X-ray-sensitive area substantially smaller than the area of said anode plate of said first scanning X-ray source and having means for producing count signals indicative of X-rays impinging on said sensitive area, at least a second additional one of said scanning X-ray sources positioned to direct X-rays towards said subject from a different angle but within the plane defined by said predetermined path of said first scanning X-ray source and said first X-ray detector, and at least a second additional one of said X-ray detectors disposed at said plane on the opposite side of said subject from said second additional scanning X-ray source, and a data processing system coupled to said scanning X-ray sources and to said detectors to receive said signals therefrom and having means for determining variations of X-ray transmissiveness at different areas of said subject from said signals.

32. Tomographic X-ray apparatus comprising:

a first scanning X-ray source having an anode plate and an electron gun for directing at least one electron beam toward said anode plate and having first beam deflection means for sweeping said electron beam relative to said anode plate to produce X-rays at successive points along a predetermined path on said anode plate, said first scanning X-ray source also having means for producing a first deflection signal which varies in accordance with the position of the moving point of impact of said electron beam on said anode plate along said predetermined path, said first X-ray source also having second beam deflection means for shifting the position of said predetermined path in a direction orthogonal thereto, a first X-ray detector spaced from said first scanning X-ray source whereby a subject to be scanned may be disposed therebetween, said first X-ray detector having at least one active X-ray-sensitive area substantially smaller than the area of said anode plate of said first scanning X-ray source and having means for producing count signals indicative of X-rays impinging on said sensitive area, at least a second additional one of said scanning X-ray sources positioned to direct X-rays towards said subject from a different angle than said first scanning X-ray source and said first X-ray detector, and at least a second additional one of said X-ray detectors disposed on the opposite side of said subject from said second additional scanning X-ray source, and a data processing system coupled to said scanning X-ray sources and to said detectors to receive said signals therefrom and having means for determining variations of X-ray transmissiveness at different areas of said subject from said signals.

* * * * *

UNITED STATES PATENT OFFICE
CERTIFICATE OF CORRECTION

Patent No. 4,144,457          Dated March 13, 1979

Inventor(s)  Richard D. Albert

It is certified that error appears in the above-identified patent and that said Letters Patent are hereby corrected as shown below:

| | |
|---|---|
| Col. 3, line 36 | "plan" should be --plane-- |
| Col. 7, line 45 | "usuable" should be --usable-- |
| Col. 8, line 49 | "chain" should be --chair-- |
| Col. 11, line 5 | "chain" should be --chair-- |
| Col. 16, line 3 | "constititues" should be --constitutes-- |
| Col. 22, line 40 | "which" should be --with-- |
| Col. 22, line 66 | "Sciene," should be --Science,-- |
| Col. 24, line 64 | "6" should be --8-- |
| Col. 31, line 27 | "gneerating" should be --generating-- |

Signed and Sealed this

Second Day of October 1979

[SEAL]

Attest:

RUTH C. MASON
*Attesting Officer*

LUTRELLE F. PARKER
*Acting Commissioner of Patents and Trademarks*